US011840708B2

(12) United States Patent
Shusta et al.

(10) Patent No.: US 11,840,708 B2
(45) Date of Patent: Dec. 12, 2023

(54) ISOGENIC BLOOD-BRAIN BARRIER MODEL

(71) Applicants: Wisconsin Alumni Research Foundation, Madison, WI (US); Cedars-Sinai Medical Center, Los Angeles, CA (US)

(72) Inventors: Eric V. Shusta, Madison, WI (US); Scott G. Canfield, Middleton, WI (US); Clive N. Svendsen, Los Angeles, CA (US); Sean P. Palecek, Verona, WI (US); Gad D. Vatine, Los Angeles, CA (US)

(73) Assignees: WISCONSIN ALUMNI RESEARCH FOUNDATION, Madison, WI (US); CEDARS-SINAI MEDICAL CENTER, Los Angeles, CA (US)

(*) Notice: Subject to any disclaimer, the term of this patent is extended or adjusted under 35 U.S.C. 154(b) by 750 days.

(21) Appl. No.: 16/091,450

(22) PCT Filed: Apr. 4, 2017

(86) PCT No.: PCT/US2017/025935
§ 371 (c)(1),
(2) Date: Oct. 4, 2018

(87) PCT Pub. No.: WO2017/176747
PCT Pub. Date: Oct. 12, 2017

(65) Prior Publication Data
US 2019/0093084 A1 Mar. 28, 2019

Related U.S. Application Data

(60) Provisional application No. 62/318,424, filed on Apr. 5, 2016.

(51) Int. Cl.
*C12N 5/071* (2010.01)
*C12N 5/0793* (2010.01)
*C12N 5/079* (2010.01)

(52) U.S. Cl.
CPC ........... *C12N 5/0697* (2013.01); *C12N 5/069* (2013.01); *C12N 5/0619* (2013.01); *C12N 5/0622* (2013.01); *C12N 2501/11* (2013.01); *C12N 2501/115* (2013.01); *C12N 2502/081* (2013.01); *C12N 2502/086* (2013.01); *C12N 2502/28* (2013.01); *C12N 2506/45* (2013.01); *C12N 2533/90* (2013.01)

(58) Field of Classification Search
CPC .. C12N 5/0697; C12N 5/0619; C12N 5/0622; C12N 5/069; C12N 2533/90; C12N 2501/11; C12N 2501/115; C12N 2506/45; C12N 2502/081; C12N 2502/086; C12N 2502/28

See application file for complete search history.

(56) References Cited

U.S. PATENT DOCUMENTS

| 8,293,495 | B2 | 10/2012 | Shusta et al. | |
| 2012/0015395 | A1 | 1/2012 | Shusta et al. | |
| 2013/0203086 | A1* | 8/2013 | Achyuta | C12M 23/16 435/7.92 |
| 2014/0127800 | A1 | 5/2014 | Shusta et al. | |
| 2017/0362584 | A1* | 12/2017 | Bani | C12N 5/069 |

FOREIGN PATENT DOCUMENTS

WO 2014/074695 A1 5/2014

OTHER PUBLICATIONS

Ebert et al. "EZ spheres: A stable and expandable culture system for the generation of pre-rosette multipotent stem cells from human ESCs and iPSCs." Stem Cell Res. May 2013 ; 10(3): 417-427 (Year: 2013).*
Rushton, David 2014. "Enhancing the function of iPS-derived neurons: implications for disease modelling." PhD Thesis, Cardiff University. I (Year: 2014).*
International Search Report and Written Opinion from PCT/US2017/025935, dated Jul. 5, 2017, 11 pages.
Ebert, et al., EZ spheres: A stable and expandable culture system for the generation of pre-rosette multipotent stem cells from human ESCs and iPSCs, Stem Cell Research, vol. 10, No. 3, May 1, 2013 (May 1, 2013), pp. 417-427.
Sareen, et al., Human induced pluripotent stem cells are a novel source of neural progenitor cells (iNPCs) that migrate and integrate in the rodent spinal cord : Human neural progenitor cells, Journal of Comparative Neurology, vol. 522, No. 12, Apr. 12, 2014 (Apr. 12, 2014), pp. 2707-2728.
Canfield, et al., An isogenic blood-brain barrier model comprising brain endothelial cells, astrocytes, and neurons derived from human induced pluripotent stem cells, Journal of Neurochemistry, vol. 140, No. 6, Feb. 14, 2017 (Feb. 14, 2017), pp. 874-888.
Azevedo et al. (2009) Equal numbers of neuronal and nonneuronal cells make the human brain an isometrically scaled-up primate brain. J Comp Neurol, 513, 532-541.
Berezowski et al. (2004) Contribution of glial cells and pericytes to the mRNA profiles of P-glycoprotein and multidrug resistance associated proteins in an in vitro model of the blood-brain barrier. Brain Res, 1018, 1-9.

(Continued)

*Primary Examiner* — Titilayo Moloye
(74) *Attorney, Agent, or Firm* — Quarles & Brady LLP

(57) ABSTRACT

A method of creating an isogenic multicellular blood-brain barrier model from iPSCs is disclosed.

26 Claims, 20 Drawing Sheets

(56) References Cited

OTHER PUBLICATIONS

Brown et al. (2015) Recreating blood-brain barrier physiology and structure on chip: A novel neurovascular microfluidic bioreactor. Biomicrofluidics, 9, 054124.

Butt et al. (1990) Electrical resistance across the blood-brain barrier in anaesthetized rats: a developmental study. J Physiol, 429, 47-62.

Calabria et al. (2008) A genomic comparison of in vivo and in vitro brain microvascular endothelial cells. J Cereb Blood Flow Metab, 28, 135-148.

Calabria et al. (2006) Puromycin-purified rat brain microvascular endothelial cell cultures exhibit improved barrier properties in response to glucocorticoid induction. J Neurochem, 97, 922-933.

Cecchelli et al. (2007) Modelling of the blood-brain barrier in drug discovery and development. Nat Rev Drug Discov, 6, 650-661.

Deli et al. (2005) Permeability studies on in vitro blood-brain barrier models: physiology, pathology, and pharmacology. Cell Mol Neurobiol, 25, 59-127.

Dohgu et al. (2005) Brain pericytes contribute to the induction and up-regulation of blood-brain barrier functions through transforming growth factor-beta production. Brain Res, 1038, 208-215.

El Hafny et al. (1997) Modulation of P-glycoprotein activity by glial factors and retinoic acid in an immortalized rat brain microvessel endothelial cell line. Neurosci Lett, 236, 107-111.

Freese et al. (2014) A novel blood-brain barrier co-culture system for drug targeting of Alzheimer's disease: establishment by using acitretin as a model drug. PLoS One, 9, e91003.

Förster et al. (2008) Differential effects of hydrocortisone and TNFalpha on tight junction proteins in an in vitro model of the human blood-brain barrier. J Physiol, 586, 1937-1949.

Herculano-Houzel et al. (2005) Isotropic fractionator: a simple, rapid method for the quantification of total cell and neuron numbers in the brain. J Neurosci, 25, 2518-2521.

Janzer et al. (1987) Astrocytes induce blood-brain barrier properties in endothelial cells. Nature, 325, 253-257.

Kim et al. (2011) Investigating synapse formation and function using human pluripotent stem cell-derived neurons. Proc Natl Acad Sci U S A, 108, 3005-3010.

Kusuma et al. (2015) Characterizing human pluripotent-stem-cell-derived vascular cells for tissue engineering applications. Stem Cells Dev, 24, 451-458.

Lim et al. (2007) Neural precursor cell influences on blood-brain barrier characteristics in rat brain endothelial cells. Brain Res, 1159, 67-76.

Lippmann et al. (2014) A retinoic acid-enhanced, multicellular human blood-brain barrier model derived from stem cell sources. Sci Rep, 4, 4160.

Lippmann et al. (2013) Modeling the blood-brain barrier using stem cell sources. Fluids Barriers CNS, 10, 2.

Lippmann et al. (2011) Blood-brain barrier modeling with co-cultured neural progenitor cell-derived astrocytes and neurons. J Neurochem, 119, 507-520.

Man et al. (2008) Human brain microvascular endothelial cells and umbilical vein endothelial cells differentially facilitate leukocyte recruitment and utilize chemokines for T cell migration. Clin Dev Immunol, 2008, 384982.

Mizee et al. (2013) Retinoic acid induces blood-brain barrier development. J Neurosci, 33, 1660-1671.

Nakagawa et al. (2009) A new blood-brain barrier model using primary rat brain endothelial cells, pericyles and astrocytes. Neurochem Int, 54, 253-263.

Nakagawa et al. (2007) Pericytes from brain microvessels strengthen the barrier integrity in primary cultures of rat brain endothelial cells. Cell Mol Neurobiol, 27, 687-694.

Perrière et al. (2007) A functional in vitro model of rat blood-brain barrier for molecular analysis of efflux transporters. Brain Res, 1150, 1-13.

Savettieri et al. (2000) Neurons and ECM regulate occludin localization in brain endothelial cells. Neuroreport, 11, 1081-1084.

Schiera et al. (2003) Synergistic effects of neurons and astrocytes on the differentiation of brain capillary endothelial cells in culture. J Cell Mol Med, 7, 165-170.

Schiera et al. (2005) Permeability properties of a three-cell type in vitro model of blood-brain barrier. J Cell Mol Med, 9, 373-379.

Stebbins et al. (2015) Differentiation and characterization of human pluripotent stem cell-derived brain microvascular endothelial cells. Methods.

Syvänen et al. (2009) Species differences in blood-brain barrier transport of three positron emission tomography radioligands with emphasis on P-glycoprotein transport. Drug Metab Dispos, 37, 635-643.

Van Der Meer et al. (2013) Three-dimensional co-cultures of human endothelial cells and embryonic stem cell-derived pericytes inside a microfluidic device. Lab Chip, 13, 3562-3568.

Warren et al. (2009) Comparative gene expression profiles of ABC transporters in brain microvessel endothelial cells and brain in five species including human. Pharmacol Res, 59, 404-413.

Weidenfeller et al. (2005) Murine brain capillary endothelial cells exhibit improved barrier properties under the influence of hydrocortisone. Brain Res, 1053, 162-174.

Weidenfeller et al. (2007) Differentiating embryonic neural progenitor cells induce blood-brain barrier properties. J Neurochem, 101, 555-565.

Weksler et al. (2005) Blood-brain barrier-specific properties of a human adult brain endothelial cell line. FASEB J, 19, 1872-1874.

Wilson et al. (2015) Exploring the effects of cell seeding density on the differentiation of human pluripotent stem cells to brain microvascular endothelial cells. Fluids Barriers CNS, 12, 13.

Yu et al. (2007) Induced pluripotent stem cell lines derived from human somatic cells. Science, 318, 1917-1920.

Zhao et al. (2015) Establishment and Dysfunction of the Blood-Brain Barrier. Cell, 163, 1064-1078.

Zlokovic et al. (2008) The blood-brain barrier in health and chronic neurodegenerative disorders. Neuron, 57, 178-201.

\* cited by examiner

FIGS. 1A-1C (CONTINUED)
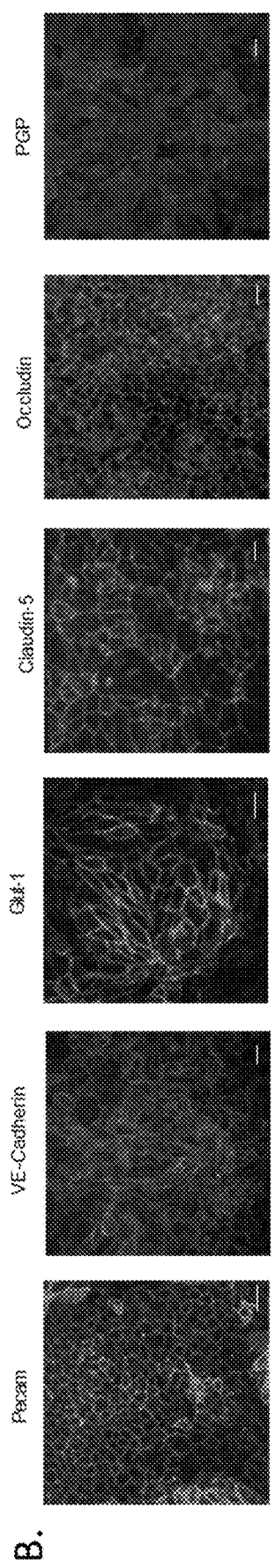
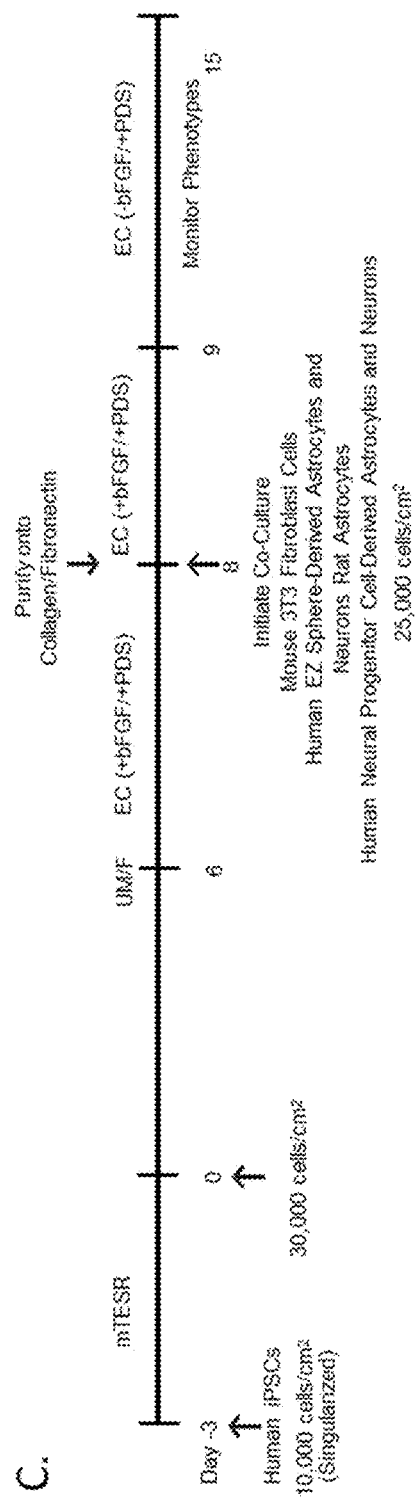

A.

B.

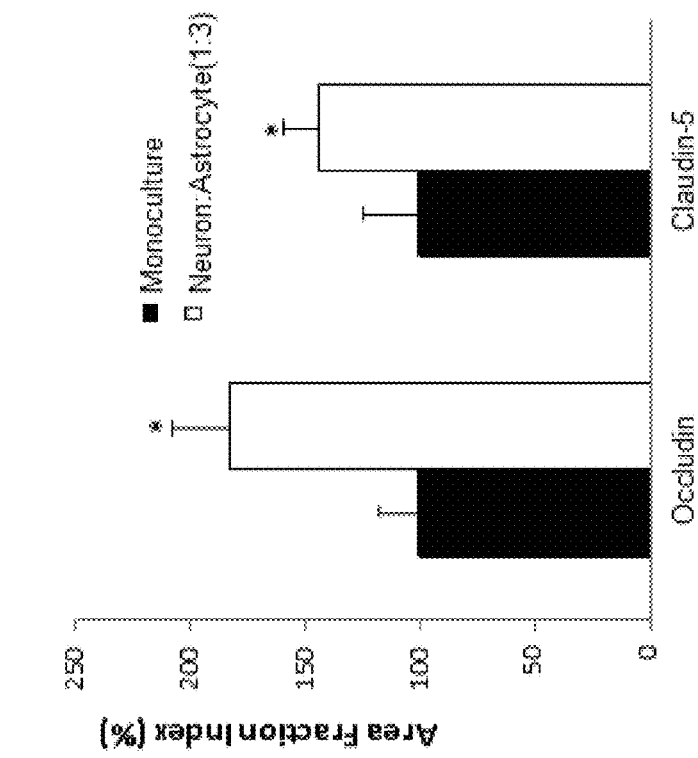
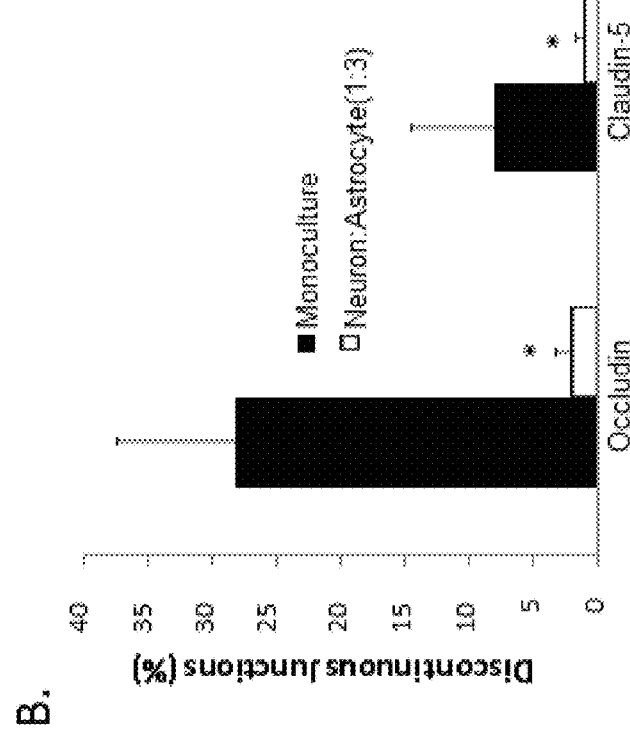
FIGS. 4A-4E (CONTINUED)

FIGS. 4A-4E (CONTINUED)
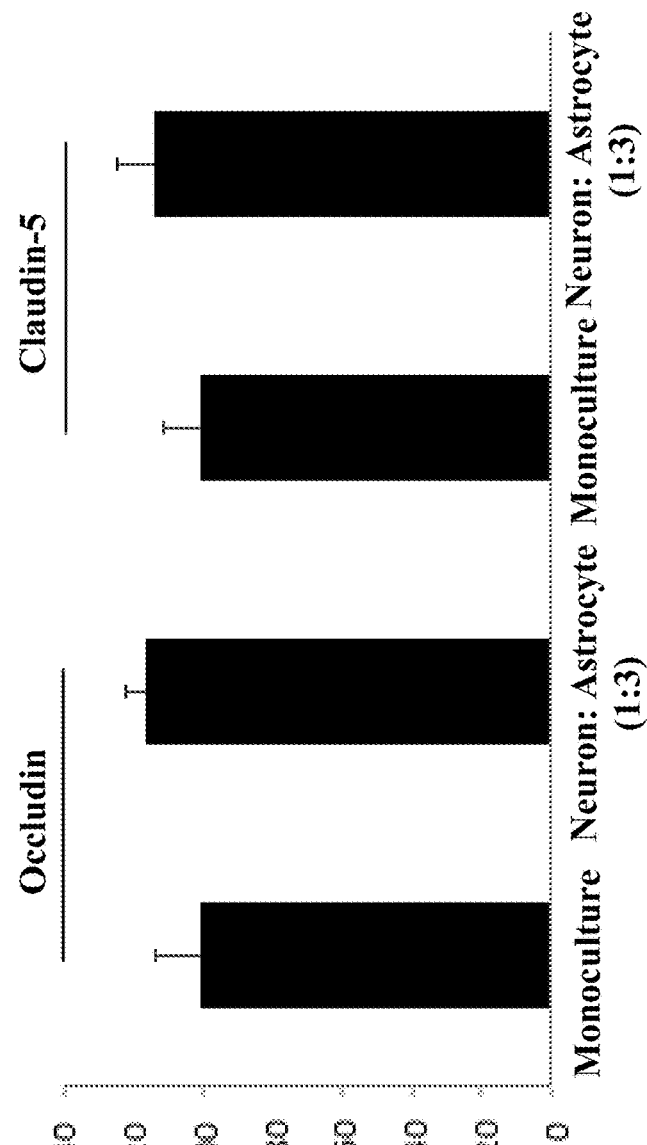
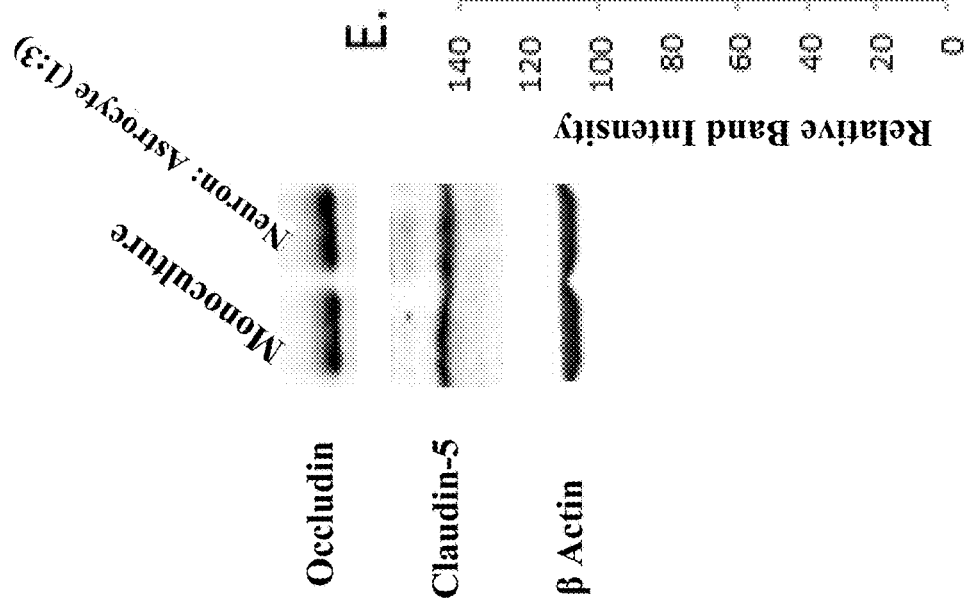

FIGS. 6A-6E (CONTINUED)
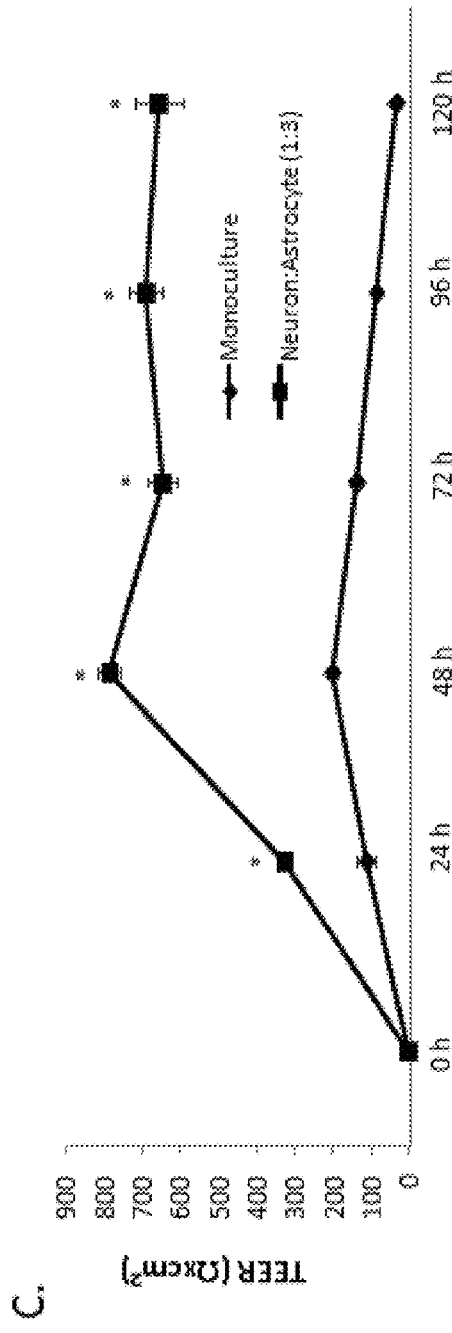
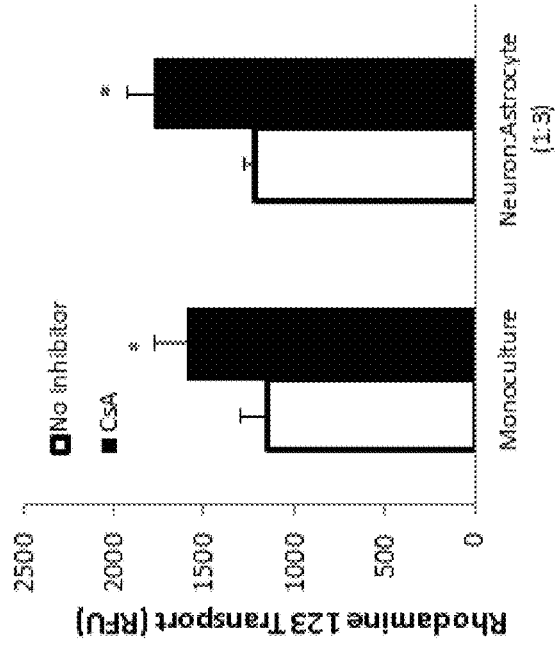
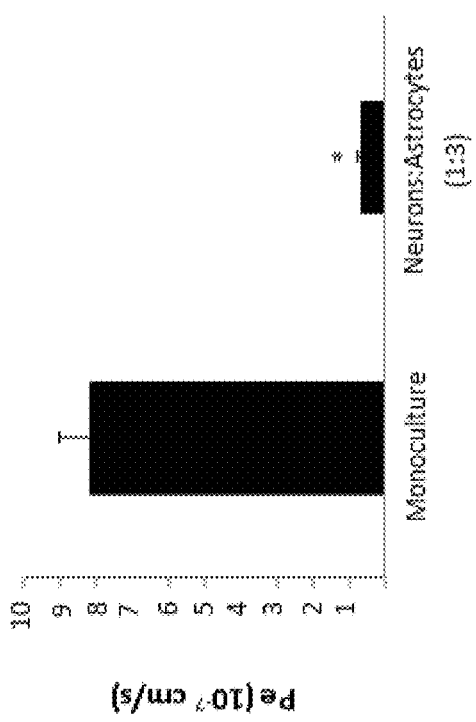

B.

ISOGENIC BLOOD-BRAIN BARRIER MODEL

CROSS REFERENCE TO RELATED APPLICATIONS

This application claims the benefit of U.S. Provisional Application 62/318,424, filed Apr. 5, 2016, which is incorporated herein in its entirety.

STATEMENT REGARDING FEDERALLY SPONSORED RESEARCH/DEVELOPMENT

This invention was made with government support under NS083688 awarded by the National Institutes of Health. The government has certain rights in the invention.

BACKGROUND

The Blood Brain Barrier (BBB) is critical for maintaining healthy brain activity and is formed by specialized endothelial cells that line the cerebral vasculature. These brain microvascular endothelial cells (BMECs) form a barrier that regulates the transport of nutrients, metabolites and cells between the blood and brain while also helping to protect the central nervous system from toxic and pathogenic insults. The barrier phenotype is elicited through the expression of a specialized cohort of tight junction proteins, efflux transporters, and nutrient transporters (Zhao et al. 2015). In healthy conditions, the BBB is effective in maintaining the delicate homeostasis between the blood and brain; however in a number of diseases, such as stroke, Alzheimer's, and ALS BBB dysfunction can play a significant role in disease progression (Zlokovic 2008).

A number of in vitro BBB models have been developed to help elucidate the role of the BBB in brain development, function, and disease, and to develop potential therapeutic approaches. Freshly isolated BMECs from various animal sources have been successfully employed, although species variations must be considered when interpreting these results and directly comparing them to a human model (Deli et al. 2005, Warren et al. 2009, Syvänen et al. 2009). Additionally, freshly isolated human BMECs or immortalized BMECs have been used to model the BBB (Cecchelli et al. 2007, Weksler et al. 2005). However, primary and transformed BMECs tend to de-differentiate and lose their barrier properties once they are removed from the brain microenvironment and often exhibit sub-par BBB phenotypes (Weksler et al. 2005, Förster et al. 2008, Man et al. 2008, Calabria & Shusta 2008).

Some of the limitations of BBB models can be mitigated by including other cells of the neurovascular unit (NVU) such as astrocytes, neurons or pericytes to help provide cues that are critical in the development, maintenance, and regulation of unique BBB properties. By creating such multi-cellular BBB models that better approximate the more complex NVU, study of BBB function in healthy and diseased states can become more representative. The primary focus of developing multicellular BBB models has been investigating the interplay between astrocytes and BMECs (Janzer & Raff 1987). Primary astrocytes in co-culture enhance BBB properties such as increased TEER and reduced permeability (Deli et al. 2005). More recently pericytes in co-culture have been shown to have similar BBB enhancing effects as astrocytes (Nakagawa et al. 2007, Lippmann et al. 2014). Neurons have also been shown to drive better localization of tight junction proteins in BMECs following co-culture (Savettieri et al. 2000, Schiera et al. 2003). The combination of all of the key cells of the NVU, in the form of BMEC co-culture with pericytes, astrocytes, and neurons has been found to be the most inductive (Nakagawa et al. 2009, Lippmann et al. 2011, Lippmann et al. 2012).

In order to leverage the power of stem cell technology in terms of scale, human sourcing, and modeling of human disease, our group recently developed a stem cell based model to differentiate human BMEC-like cells (Lippmann et al. 2012, Wilson et al. 2015). These iPSC-BMECs exhibit a number of critical BBB characteristics including elevated Trans-endothelial electrical resistance (TEER), reduced fluorescein permeability, active efflux transporters, nutrient transporters, and tight junction protein expression (Wilson et al. 2015, Lippmann et al. 2012, Lippmann et al. 2014, Lippmann et al. 2013). In addition, we demonstrated that co-culture with NVU cells including primary human pericytes, astrocytes, and neurons in various combinations can induce BBB properties such as barrier tightening in iPSC-BMECs as well (Lippmann et al. 2014, Lippmann et al. 2012). However, the co-cultured NVU cells were of primary origin and hence limited in scale and accessibility. Moreover, an isogenic human NVU model derived from the same human patient could provide substantial benefits in the study of healthy and diseased patients.

There is a need in the art for an improved BBB model made entirely from hPSCs.

DESCRIPTION OF DRAWINGS

The patent or patent application file contains at least one drawing in color. Copies of this patent or patent application publication with color drawings will be provided by the Office upon request and payment of the necessary fee.

SUMMARY OF THE INVENTION

Figures 1A, 1B, 1C:
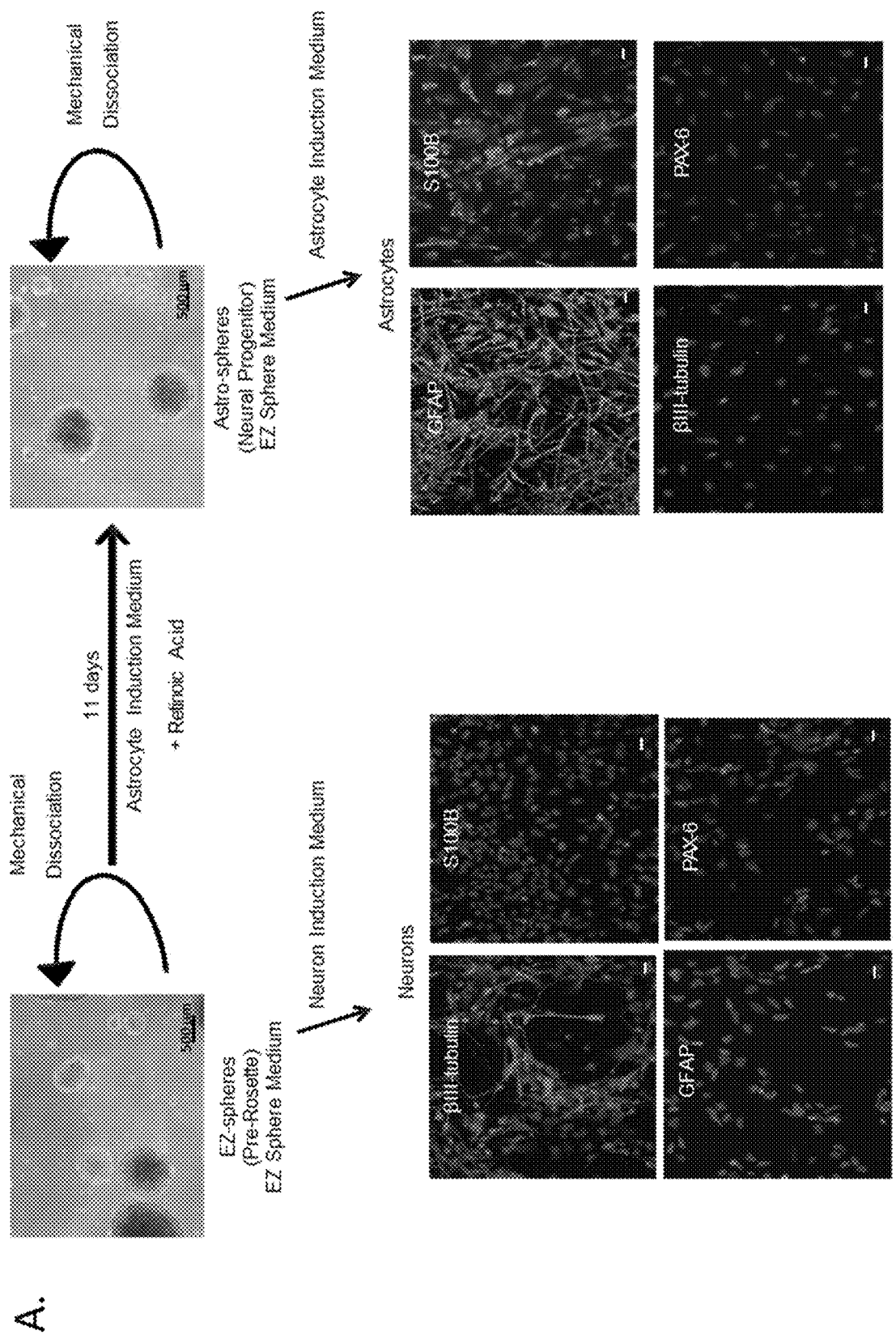
FIGS. 1A-1C show derivation of neurons, astrocytes and BMECs for BBB modeling. (A) iPSC 4.2 EZ-spheres were maintained in suspension in EZ sphere medium. EZ-spheres were singularized and differentiated towards neurons following a 14-day treatment with neuron induction medium. EZ-spheres were also differentiated further to an astrosphere population following an 11-day treatment with astrocyte induction medium supplemented with retinoic acid. Astrospheres were maintained in suspension in EZ sphere medium and subsequently differentiated to astrocytes following 14 days in an astrocyte induction medium. To examine neuronal and astrocyte differentiation, EZ-sphere-derived cell populations were immunocytochemically labeled for the early neural ectoderm marker PAX-6, neuronal marker β-III tubulin, and astrocyte markers S100B and GFAP. Scale bar=200 μm. To derive BMECS, singularized IMR90-4 iPSCs were expanded for 3 days prior to the initiation of differentiation (Day 0), differentiated for six days in UM/F medium and then switched to an EC based medium for two days. (B) IMR90-4 iPSC-derived BMECs were immunolabeled for PECAM-1 (platelet-endothelial cell adhesion molecule-1) and VE-Cadherin, the glucose transporter Glut-1, tight junction proteins Claudin-5 and Occludin, and the efflux transporter PGP. Scale bars=100 μm. (C) iPSC-BMEC differentiation and co-culture timeline. Day 8 differentiated BMECs were placed in co-culture with EZ-sphere-derived astrocytes or neurons or control cell types including rat astrocytes, human neural progenitor cell-derived astrocytes and neurons, mouse 3T3 fibroblasts. All co-culture experiments were conducted in EC medium with BBB phenotypes being monitored to day 15.

In one embodiment, the present invention is a method of differentiating induced pluripotent stem cells (iPSC) to neurons, the method comprising the steps of: i) differentiating the iPSCs into EZ-spheres; ii) singularizing the EZ-spheres; iii) seeding the singularized EZ-spheres on to an extracellular matrix; and iv) culturing the seeded EZ-spheres in a neural medium, wherein neurons are formed, and wherein the neurons express β-tubulin III. In a preferred version of the invention, the neural medium comprises DMEM/F12, penicillin-streptomycin antibiotic, B27 minus vitamin A, and heparin. In another preferred version of the invention, the seeding density is 20,000-30,000 cell/cm².

In another version, the present invention is a method of differentiating induced pluripotent stem cells (iPSC) to astrocytes, the method comprising the steps of: i) differentiating the iPSCs into EZ-spheres; ii) treating the EZ-spheres with a neural induction medium to produce astro-spheres; iii) culturing the astro-spheres, wherein the cells are passaged weekly; iv) singularizing the astro-spheres; v) seeding the singularized astro-spheres on an extracellular matrix; and vi) culturing the seeded astro-spheres in medium comprising DMEM/F12, NEAA, N2 and heparin, wherein astrocytes are formed, and wherein astrocytes express glial fibrillary acidic protein and S100 calcium binding protein B. In a preferred version, the neural induction medium comprises DMEM/F12, NEAA, N2 (neural supplement), heparin, and all-trans retinoic acid. In another preferred version, the seeding density is 20,000-30,000 cell/cm².

In another version, the present invention is inducing blood brain barrier properties in iPSC-derived brain microvascular endothelial cells (BMECs) to generate an isogenic blood brain barrier model by a method comprising (a) co-culturing iPSC-derived BMECs with a cell type selected from the group consisting of iPSC-derived astrocytes, iPSC-derived neurons, and combinations thereof, wherein the astrocytes and neurons are created by the methods of claims 1 and 6; wherein blood brain barrier properties are induced, and wherein the iPSC-derived astrocytes and iPSC-derived neurons are isogenic to the iPSC-derived BMECs.

DESCRIPTION OF THE INVENTION

In general, preferred embodiments of the present invention include (1) an isogenic blood brain barrier (BBB) model derived from renewable pluripotent stem cells from a single source, (2) a method of cell differentiation, and (3) a method of creating an isogenic BBB model.

The term "isogenic" as used herein, refers to cells originating or differentiated from the same subject or same line of human pluripotent stem cells (hPSCs). The cells are not exposed to cells of an alternate genetic origin as the model is being prepared. The prior art discloses methods of creating BBBs with cell types derived from iPS cells and varying primary cell sources but does not disclose an isogenic BBB. In the present invention, hPSC derived astrocytes and neurons are co-cultured with BMECs derived from the same hPSC source to create an isogenic blood brain barrier model.

In a previous U.S. patent application (Ser. No. 13/155, 435, U.S. Patent Publication No. 2012/0015395, incorporated herein by reference), Applicants demonstrated that human pluripotent stem cells could be differentiated into brain microvascular endothelial cells (BMECs). In U.S. Pat. No. 8,293,495, incorporated herein by reference, Applicants demonstrated that astrocytes and neurons derived from human neural progenitor cells (primary/non-stem cell) can induce BBB properties in cultured rodent BMECs. In another previous U.S. patent application (Ser. No. 13/793, 466, U.S. Patent Publication No. 2014/0127800, incorporated herein by reference), Applicants demonstrated that the hPSC and hNPC systems can be combined to create a fully-human BBB co-culture model.

Unless defined otherwise, all technical and scientific terms used herein have the same meanings as commonly understood by one of ordinary skill in the art to which this invention belongs.

In the specification and in the claims, the terms "including" and "comprising" are open-ended terms and should be interpreted to mean "including, but not limited to." These terms encompass the more restrictive terms "consisting essentially of" and "consisting of." It is also to be noted that the terms "comprising," "including," "characterized by" and "having" can be used interchangeably.

As used herein and in the appended claims, the singular forms "a," "an," and "the" include plural reference unless the context clearly dictates otherwise. As well, the terms "a" (or "an"), "one or more" and "at least one" can be used interchangeably herein.

Where a range of values is provided, it is understood that each intervening value, and any combination or sub-combination of intervening values, between the upper and lower limit of that range and any other stated or intervening value in that stated range, is encompassed within the range of values recited.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number, and thus will typically refer to a number or value that is 10% below or above the specifically recited number or value.

The term "sub-culture phase" as used herein, refers to a monoculture of hPSC-derived cells, preferably hPSC-derived BMECs, hPSC-derived EZ-spheres, hPSC-derived neurons, or hPSC-derived astrocytes. The term "co-culture phase" as used herein, refers to a phase where hPSC-derived BMECs are cultured with hPSC-derived neurons and astrocytes or other cell types.

An isogenic blood brain barrier (BBB) of the present invention will typically be constructed as described below. hPSCs, human pluripotent stem cells, may be obtained from many sources. The cells can include human embryonic stem cells (hESCs) or induced pluripotent stem cells (iPSCs). Preferred sources for hPSCs include those hESCs derived from blastocysts or morulas and those iPSCs reprogrammed from any somatic cell type, preferably fibroblasts. In a preferred embodiment, iPSCs are used.

hPSCs are differentiated to BMECs as previously described (U.S. Patent Publication 2012/0015395, incorporated herein by reference). In a preferred method of differentiating iPSCs to BMECs, iPSCs were singularized using ACCUTASE solution and single cell seeded on plates coated with an extracellular matrix at a seeding density of about 10,000 cells/cm$^2$. In one embodiment, the extracellular matrix is MATRIGEL™. When the cell density reaches about 30,000 cells/cm$^2$, medium was replaced with unconditioned medium (UM) containing knock-out serum replacement, non-essential amino acids, GLUTA-MAX, β-mercaptoethanol, and DMEM/F12. After 6 days in UM medium, cells are treated with endothelial cell (EC) medium containing hESFM, with basic fibroblast growth factor and platelet-derived bovine serum for two days. A preferred EC medium is EC medium containing 200 mL hESFM (Life Technologies) supplemented with 20 ng/mL basic fibroblast growth factor (bFGF; WiCell) and 1% platelet-derived bovine serum (Biomedical Technologies, Inc.).

Cells are then sub-cultured with ACCUTASE solution onto collagen IV and fibronectin in sterile water at a density of 1×10$^6$ cells/cm2 on a TRANSWELL permeable membrane insert. After 24 hours in EC medium, BMECs are switched to EC medium without bFGF.

EZ-spheres can be derived from hPSCs as previously described (Ebert et al. 2013, Stem Cell Res. 10(3):417-427 and Sareen et al. 2014, Journal of Comparative Neurology, both incorporated herein by reference). EZ-spheres are a self-renewing pre-rosette neural stem cell population that can be cultured in suspension for prolonged periods of time, passaged via chopping techniques, and differentiated toward a range of central and peripheral neural lineages. In one embodiment, EZ-spheres are derived from iPSCs. In the sub-culture phase EZ-spheres are maintained with EZ-sphere medium containing BFGF, epidermal growth factor, and heparin, and are passaged weekly.

In a preferred method to differentiate EZ-spheres into neurons to produce hPSC-derived neurons, EZ-spheres may be singularized using ACCUTASE solution and seeded onto extracellular matrix coated plates. Cells may be cultured in neural medium consisting of DMEM/F12 supplemented with 1% penicillin-streptomycin antibiotic, 2% B27 minus vitamin A, and heparin. In one embodiment, the seeding density is between 20,000 and 30,000 cells/cm$^2$. In a preferred embodiment, the seeding density is about 25,000 cell/cm$^2$. In a preferred embodiment, the extracellular matrix is MATRIGEL™. In one embodiment cells are differentiated for 10-18 days. In a preferred embodiment, cells are differentiated for 14 days. Neurons differentiated from EZ-spheres express β-tubulin III, and are completely absent of any expression of glial fibrillary acidic protein or S100 calcium binding protein B or paired box protein-6. Neurons may also express nestin.

In a preferred method to differentiate EZ-spheres into astrocytes to produce hPSC-derived astrocytes, EZ-spheres may be treated with a neural induction medium consisting of DMEM/F12 supplemented with NEAA, N2 neural supplement, heparin and all-trans retinoic acid to form astrospheres. In one embodiment, cells are treated for 10-13 days. In a preferred embodiment, cells are treated for 11 days.

Astro-spheres may then be returned to EZ-sphere medium to be passaged weekly. In a preferred embodiment, the astro-spheres are passaged via the chopping method. Astrospheres may be singularized with ACCUTASE solution and seeded onto extracellular matrix coated plates and cultured in astrocyte medium consisting of DMEM/F12 with NEAA, N2, and heparin. In one embodiment, the seeding density is between 20,000 and 30,000 cells/cm$^2$. In a preferred embodiment, the seeding density is about 25,000 cell/cm$^2$. In a preferred embodiment, the extracellular matrix is MATRIGEL™. In one embodiment cells are differentiated for 10-18 days. In a preferred embodiment, cells are differentiated for 14 days. Astrocytes differentiated from EZ-spheres express glial fibrillary acidic protein and S100 calcium binding protein B, and are completely absent of any expression of paired box protein-6 or β-tubulin III. Astrocytes may also express nestin.

MATRIGEL™ is a mixture of extracellular matrix proteins and growth factors derived from Engelberth-Holm-Swarm tumor basement membranes. MATRIGEL™ could be replaced with any matrix that presents the necessary combination of growth factors and matrix proteins.

In a preferred method of generating a blood brain barrier model, hPSC-derived BMECs are co-cultured with hPSC-derived neurons, astrocytes or combinations thereof immediately following the BMEC sub-culture phase. For co-cultures, iPSC-derived BMECs are plated on membranes at a density of 1,000,000 cell/cm$^2$ and sub-cultured in EC (+PDS, +bFGF) medium. In the membrane co-culture system, BMECs can be seeded onto the top of the membrane, while other co-culture cell types are plated below the membrane on the surface of the culture plate. In a preferred embodiment, the membranes are Transwell membranes, which are porous (0.4 micron) inserts that allow for interaction between the BMECs and co-culture subtypes.

After 24 hours, the medium is changed to EC medium without bFGF. The iPSC-derived BMECs are suspended in a co-culture immediately following sub-culture onto TRANSWELL membranes with iPSC-derived neurons, iPSC-derived astrocytes, or mixtures thereof, which are seeded on an extracellular matrix. In a most preferred embodiment the ratio of neurons to astrocytes is 1:3, +/−10%.

Co-culture of iPSC-derived BMECs with iPSC-derived neurons, iPSC-derived astrocytes, or mixtures thereof, will produce an isogenic blood brain barrier model with properties as generally characterized below.

The trans-endothelial electrical resistance (TEER) of the BBB model can be measured by any known means in the art.

TEER may be recorded using an EVOM voltohmmeter with STX2 electrodes and is preferably measured every 24 hours following initiation of the co-culture phase. In one embodiment, the TEER of the BBB model is between 400-1000 $\Omega \times cm^2$. In a preferred embodiment, the TEER of the BBB model is between 500 and 950 $\Omega \times cm^2$. In a most preferred embodiment, the TEER of the BBB model is between 600 and 900 $\Omega \times cm^2$.

Immunocytochemistry characterization of the tight junctions of the BBB model can be conducted by any means known in the art. In a preferred embodiment immune-labeling of occludin and claudin-5 is used to quantify tight junctions. In one embodiment, the percentage of discontinuous junctions in the BBB model is between 0-8%. In a preferred embodiment, the percentage of discontinuous junctions in the BBB model is between 0-5%. In a most preferred embodiment, the percentage of discontinuous junctions is between 0-2%.

Protein transporter assays to characterize the hPSC-derived cells or the BBB model can be conducted by any means known in the art. In a preferred embodiment PGP efflux transporter activity is measured using the flux of rhodamine 123 with and without the PGP inhibitor, Cyclosporin A (CsA). In one embodiment, the percentage of rhodamine 1,2,3 transport with CsA inhibition is 20-60% above no-inhibition. In a preferred embodiment, the percentage of rhodamine 1,2,3 transport with CsA inhibition is 40-60% above no-inhibition.

Permeability measurements to characterize the BBB model can be conducted by any means known in the art. In a preferred embodiment, sodium fluorescein is used to measure permeability. In one embodiment, the fluorescein permeability of the BBB model is between 0.1 and $6 \times 10^{-7}$ cm/s. In a preferred embodiment, the permeability of the BBB model is between 0.1 and $4 \times 10^{-7}$ cm/s. In a most preferred embodiment, the permeability of the BBB model is between 0.1 and $2 \times 10^{-7}$ cm/s.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions of the novel methods of the present invention are to be regarded as illustrative in nature and not restrictive.

EXAMPLES

Example 1

The blood brain barrier (BBB) is key for healthy brain activity and is formed by specialized endothelial cells that line the cerebral vasculature. These brain microvascular endothelial cells (BMECs) form a barrier that regulates the transport of nutrients, metabolites and cells between the blood and brain while also helping to protect the central nervous system from toxic and pathogenic insults. The barrier phenotype is elicited through the expression of a specialized cohort of tight junction proteins, efflux transporters, and nutrient transporters (Zhao et al. 2015). In healthy conditions, the BBB is effective in maintaining the delicate homeostasis between the blood and brain; however in a number of diseases, such as stroke, Alzheimer's, and ALS, BBB dysfunction can play a significant role in disease progression (Zlokovic 2008).

A number of in vitro BBB models have been developed to help elucidate the role of the BBB in brain development, function, and disease, and to develop potential therapeutic approaches. Freshly isolated BMECs from various animal sources have been successfully employed, although species variations must be considered when interpreting these results and comparing them to the human condition (Deli et al. 2005, Warren et al. 2009, Syvänen et al. 2009). Additionally, freshly isolated human BMECs and immortalized BMECs have been used to model the BBB (Cecchelli et al. 2007, Weksler et al. 2005). However, primary and transformed BMECs tend to de-differentiate and have decreased barrier properties once they are removed from the brain microenvironment (Weksler et al. 2005, Förster et al. 2008, Man et al. 2008, Calabria & Shusta 2008).

Some of the limitations of BBB models can be mitigated by including other cells of the neurovascular unit (NVU) such as astrocytes, neurons or pericytes to help provide cues that are critical in the development, maintenance, and regulation of unique BBB properties. By creating such multicellular in vitro BBB models that better approximate the more complex NVU, study of BBB function in healthy and diseased states can become more representative of in vivo BBB physiology. A main focus of developing multicellular BBB models has been investigating the interplay between astrocytes and BMECs (Janzer & Raff 1987). Primary astrocytes in co-culture enhance BBB properties, including increased TEER and reduced paracellular permeability (Deli et al. 2005). More recently, pericytes in co-culture have been shown to have similar BBB enhancing effects to astrocytes (Nakagawa et al. 2007, Lippmann et al. 2014). Neurons have also been shown to stimulate continuous tight junction formation in BMECs following co-culture (Savettieri et al. 2000, Schiera et al. 2003, Brown et al. 2015). Moreover, the multicellular combination of pericytes, astrocytes, and neurons has been found to induce BMEC phenotypes more significantly than any single co-cultured cell type (Nakagawa et al. 2009, Lippmann et al. 2011, Lippmann et al. 2012, Brown et al. 2015).

To address properties such as scale, human sourcing, and human disease modeling as they relate to in vitro BBB models, our group developed an approach to differentiate human iPSCs to BMEC-like cells (Lippmann et al. 2012, Wilson et al. 2015). These iPSC-derived endothelial cells exhibit a number of important BBB characteristics including elevated trans-endothelial electrical resistance (TEER), reduced fluorescein permeability, active efflux transporters, and the expression of nutrient transporters and tight junction proteins (Wilson et al. 2015, Lippmann et al. 2012, Lippmann et al. 2014, Lippmann et al. 2013). Since other peripheral endothelia can also express some of the markers and phenotypes characteristic of BMECs, we refer to these iPSC-derived cells as being BMEC-like (abbreviated as iPSC-derived BMECs) (Lippmann et al. 2012, Wilson et al. 2015). In addition, we demonstrated that co-culture with NVU cells including primary human brain pericytes, astrocytes, and neurons in various combinations induced BBB properties such as barrier tightening in iPSC-derived BMECs (Lippmann et al. 2014, Lippmann et al. 2012). However, the co-cultured NVU cells were of primary origin, and hence limited in scale and accessibility.

In the embodiment described in this Example, we differentiated iPSCs to astrocytes and neurons that are capable of inducing BBB phenotypes in isogenic iPSC-derived BMECs. Such an isogenic human NVU model derived from the same human donor provides substantial benefits in the study of BBB structure and function in healthy and diseased patients. To this end, we employed EZ spheres, a stable and expandable pluripotent stem cell-derived neural stem cell-like aggregate system (Ebert et al. 2013, Sareen et al. 2014). iPSC-derived EZ spheres retain their potential to form neural rosettes following prolonged cultures and can be differentiated into various neural and glial lineages (Ebert et al. 2013). We demonstrate herein that primary or iPSC-derived BMECs in co-culture with EZ sphere-derived astrocytes and/or neurons exhibit reduced permeability and improved tight junction localization compared to BMECs in monoculture. Furthermore, iPSC-derived astrocytes and neurons increased BMEC TEER to greater levels than co-culture with primary human NPC-derived astrocytes and neurons, or rat astrocytes. Finally, we demonstrate herein the capability for isogenic NVU modeling by employing BMECs, astrocytes and neurons differentiated from the same patient-derived iPSC line.

Materials and Methods iPSC Differentiation to BMECs—IMR90-4 (WiCell) and CSO3iCTRn2 (Cedars Sinai iPSC-Core) iPSCs were cultured between passages 32-56 on Matrigel™ (BD Biosciences) and supplemented daily with mTESR™1 medium (WiCell) as previously described (Stebbins et al. 2015, Yu et al. 2007). iPSC line, CSO3iCTRn2 was generated at Cedars Sinai iPSC-Core and was verified for pluripotency markers, array based Pluri-Test, and G-band karyotype analysis. iPSCs were passaged every 3-4 days with Versene (Life Technologies) at a typical ratio of 1:12. BMECs were differentiated following seeding of iPSCs singularized with Accutase (Life Technologies) at a seeding density of 10,000 cells/cm$^2$ and expanded to 30,000 cells/cm$^2$ (2-3 days) (Wilson et al. 2015). Once the optimal density (30,000 cells/cm$^2$) was reached, medium was replaced with unconditioned medium (UM: 100 mL Knock-out serum replacement (Life Technologies), 5 mL non-essential amino acids (Life Technologies), 2.5 mL of gluta-max (Life Technologies), 3.5 µL of β-mercapto-ethanol (Sigma), and 392.5 mL of DMEM/F12 (1:1) daily for six days. UM was then replaced with EC medium containing 200 mL hESFM (Life Technologies) supplemented with 20 ng/mL basic fibroblast growth factor (bFGF; WiCell) and 1% platelet-derived bovine serum (Biomedical Technologies, Inc.) for two days. Cells were then dissociated into single cells with Accutase and plated onto collagen IV (400 µg/mL; Sigma) and fibronectin (100 µg/mL; Sigma) in sterile water at a density of 1×10$^6$ cells/cm$^2$ on 1.12 cm$^2$ Transwell-Clear permeable inserts (0.4 µm pore size; Corning) or at a density of 250,000 cells/cm$^2$ on 12-/24-/96-well tissue culture polystyrene plates (Corning). The first 24 h following the subculture of the BMECs, the cells were cultured in EC medium and then switched to EC medium lacking bFGF for the duration of the experiments.

iPSC Differentiation to EZ-Sphere Derived Neurons and Astrocytes—4.2 (GM003814 Coriell Institute) and CSO3iCTRn2 iPSCs were differentiated into EZ spheres by lifting intact iPSC colonies with collagenase (1 mg/mL, Gibco) in an ultra-low attachment flask (Yu et al. 2007). EZ spheres were fed every other day with an EZ-sphere medium consisting of DMEM/F12 supplemented with 100 ng/mL bFGF, 100 ng/mL epidermal growth factor (EGF, Pepro-tech), and 5 µg/mL heparin (Sigma) and passaged weekly using a mechanical dissociation technique. EZ-sphere differentiation to neurons: EZ spheres were singularized with Accutase and seeded at 25,000 cells/cm$^2$ onto Matrigel™ coated plates. Cells were cultured in neuron medium consisting of DMEM/F12 (70:30; Life Technologies) supplemented with 1% penicillin-streptomycin, 2% B27 minus vitamin A (Life Technologies) and 2 µg/mL heparin for two weeks with medium changes every other day (Ebert et al. 2013). EZ-sphere differentiation to astrocytes: EZ spheres were treated with a astrocyte induction medium consisting of DMEM/F12 supplemented with 1% NEAA, 1% N2 (neural supplement), heparin (2 ug/mL) and all-trans retinoic acid (RA, 0.5 µM) for 11 days with daily medium changes and were renamed astrospheres, due to their propensity to differentiate into astrocytes. The astrospheres could then be transferred back to EZ-sphere medium and passaged weekly with mechanical dissociation. Astrospheres could be singularized with Accutase and plated onto Matrigel™-coated plates at a density of 25,000 cells/cm$^2$ and cultured in astrocyte medium consisting of DMEM/F12 (1:1, Life Technologies) with 1% NEAA, 1% N2, and 2 µg/mL heparin for two weeks with medium changes every other day (Sareen et al. 2014).

Isolation of Rat BMECs—All animal work was performed using protocols approved by the University of Wisconsin-Madison Animal Care and Use Committees and following NIH guidelines for care and use of laboratory animals. Rat brain capillaries were isolated from adult male Sprague Dawley rats (Harlan). The brain tissue was minced and digested in collagenase type-2 (0.7 mg/mL) and DNAse I (39 U/mL). Following centrifugation in 20% bovine serum albumin, the purified microvessel pellet was digested further in 1 mg/mL collagenase/dispase and DNAse I. To obtain a pure capillary population, we utilized a 33% Percoll gradient and plated the cells onto collagen IV/fibronectin-coated Transwells. Capillaries were cultured in DMEM supplemented with 20% PDS, 1 ng/mL bFGF, 1 µg/mL heparin, 2 mM L-glutamine, and 1% antibiotic-antimycotic solution. Pure BMEC monolayers were obtained by treating the cells with puromyocin (4 µg/mL) for two days following seeding. Co-culture experiments began ~4 days following isolation at which point the BMECs had reached confluence (Calabria et al. 2006).

Isolation of Rat Astrocytes—Astrocytes were harvested as previously described (Weidenfeller et al. 2007). P6 neonatal rat's cortices were collected and minced in HBSS medium. Trypsin (5 mg/mL) was utilized to digest the cortices for 25 min at 37° C., followed by 5 minutes of DNAse I (114 U/mL). The digested tissue was filtered through a 70 um mesh strainer and seeded at a density of 2.5×10$^4$ cells/cm$^2$ in collagen I (50 µg/mL) coated flasks. Astrocytes were cultured in DMEM supplemented with 10% fetal bovine serum, 10% horse serum, L-glutamine (2 mmol/L) and 1% antibiotic-antimycotic.

Culture of 3T3 Fibroblasts and NPCs—3T3 mouse fibroblast cells (ATCC) were cultured in DMEM supplemented with 10% FBS with daily medium changes. Mouse 3T3 cells were utilized as a non-neural cell control in the co-culture experiments. Human NPCs were maintained in medium consisting of DMEM/F12 (70:30, Life Technologies) supplemented with 2% B27, 1% antibiotic-antimycotic, 20 ng/mL bFGF, 20 ng/mL EGF, 10 ng/mL leukemia inhibitor factor (LIF; Millipore) and 5 µg/mL heparin (Lippmann et al. 2011). NPCs were passaged every week via mechanical dissociation. NPCs were differentiated to approximately 1:3 neurons:astrocytes by seeding Accutase-singularized cells onto poly-L-lysine (Sigma) coated flasks and culturing in NPC maintenance medium lacking the growth factors and supplemented with 1% FBS for 12 days (Lippmann et al. 2011).

Initiation of Co-Culture Experiments—Co-cultures were executed in a similar fashion in all experiments unless otherwise stated. Immediately following the sub-culture stage of the iPSC-BMECs, BMECs were maintained as either a monoculture or co-culture with human stem cell-derived astrocytes, neurons, or varying combinations, 3T3 fibroblasts, primary human NPC-derived astrocytes and neurons, or rat astrocytes. All experimental co-culture groups were seeded at 25,000 cells/cm² prior to the initiation of co-culture. BMECs were seeded onto Transwells and all co-culture subtypes were seeded below the Transwells onto the plate surface. For 24 h following the subculture of iPSC-BMECs onto Transwells, all cells were cultured in EC medium (+PDS/+bFGF) and then transitioned to EC medium (+PDS/−bFGF) for the remainder of all experiments. Additional co-culture media were tested: DMEM/F12 medium (+10% FBS), EC medium (+10% FBS), EC medium (+1% FBS), EC medium/DMEM/F12 medium (+10% FBS) 50:50 mix; all experimental medium conditions resulted in viable cells, however the greatest barrier tightening was observed when EC medium (+PDS/+bFGF) was utilized for the first 24 h of co-culture, and then transitioned to EC medium (+PDS/−bFGF). The initiation of co-culture of rat BMECs with human iPSC-derived astrocytes and neurons occurred four days following rat BMEC isolation. Co-culture experiments employing rat BMECs were conducted in the rat BMEC medium previously described.

Resistance Measurements—Trans-endothelial electrical resistance (TEER) was measured every 24 h following the sub-culture of BMECs. Resistance was recorded using an EVOM ohmmeter with STX2 electrodes (World Precision Instruments). TEER values were presented as Ω×cm² following the subtraction of an un-seeded Transwell and multiplication by 1.12 cm² to account for the surface area. TEER measurements were measured three independent times on each sample and at least from three triplicate filters for each experimental condition.

Immunocytochemistry and Analysis of Tight Junctions—Immunocytochemistry was conducted on iPSC-BMECs following mono/co-culture conditions and on all experimental groups utilized in co-culture experiments as previously described (Stebbins et al. 2015). Primary antibody sources and dilutions are provided in Table 1. Cells were fixed in cold methanol (100%, Sigma) for 15 min. Cells were blocked in 10% goat serum (Sigma) for 30 min at room temperature. Images were taken on Olympus epifluorescence microscope. Primary antibodies, dilution ratios, fixation and blocking agents were previously described (Stebbins et al. 2015). Discontinuous tight junctions were quantified in occludin and claudin-5 immuno-labeled BMECs following monoculture or co-culture with iPSC-derived neurons and astrocytes (1:3 ratio). Following immunostaining with occludin or claudin-5, cells that lacked at least one continuous junction were classified as discontinuous. Images were processed in Image J with a minimum of ten fields with approximately 30 cells/field from three separate differentiations were quantified and all experimental groups remained blinded until completion of the study. Using the same images, the area of each image that exhibited occludin or claudin-5 immunoreactivity was measured to determine the area fraction index.

TABLE 1

| Target Antigen | Antibody Species | Vendor | Clone/Product Number | Dilution* |
|---|---|---|---|---|
| Pecam-1 | Rabbit | Thermo Scientific | RB-10333 | 1:25 |
| VE-Cadherin | Mouse | Santa Cruz | F-B | 1:100 |
| Glut-1 | Mouse | Thermo Scientific | SPM498 | 1:500 |

TABLE 1-continued

| Target Antigen | Antibody Species | Vendor | Clone/Product Number | Dilution* |
|---|---|---|---|---|
| Claudin-5 | Mouse | Life Technologies | 4C3C2 | 1:200 (FC) 1:200 1:500 (WB) |
| Occludin | Mouse | Life Technologies | OC-3F10 | 1:50 1:500 (WB) |
| P-glycoprotein | Mouse | Thermo Scientific | P170 (F4) | 1:25 (FC) |
| Multidrug resistance-asociated protein 1 | Mouse | Millipore | MAB4100 | 1:25 (FC) |
| Breast Cancer resistance protein | Mouse | Millipore | MAB4155 | 1:50 1:25 (FC) |
| Transferrin Receptor | Mouse | R&D | MAB2474 | 1:200 (FC) |
| Nestin | Mouse | Millipore | 10C2 | 1:500 |
| Beta-III-tubulin | Rabbit | Sigma | T3952 | 1:500 1:3000 (FC) |
| Glial fibrillary acidic protein | Rabbit | Dako | ZO334 | 1:500 1:5000 (FC) |
| Pax-6 | Mouse | Developmental Studies | 1C8 | 1:100 |
| S100B | Mouse | Abcam | 11178 | 1:200 |

*Dilutions given are ideal for immuno-chemistry unless otherwise noted, WB = western blot, FC = flow cytometry.

Western Blot—BMECs were rinsed 1× with PBS and lysed using ice-cold RIPA buffer with protease inhibitor cocktail (Pierce). Lysates were quantified for protein concentration using a BCA assay (Pierce) and loaded into 4-12% Tris-Glycine SDS-PAGE gels (Invitrogen). After transferring samples onto nitrocellulose membranes, the membranes were washed one time with Tris-buffered saline with 0.1% Tween 20 (TBST) and blocked for 1 h in blocking buffer (5% non-fat dry milk dissolved in TBST). Membranes were then probed overnight at 4° C. with primary antibodies (Table 1) in blocking buffer. Membranes were washed 3× with 5 mL of TBST, then incubated 10 min with 10 mL of TBST, followed by aspiration of the TBST and incubation of blots again with 10 mL of TBST for 5 min (wash step). Membranes were probed with secondary antibodies diluted in blocking buffer for 1 h at room temperature in the dark (1:5000 donkey anti-mouse IRDye 800CW, LICOR; 1:5000 donkey anti-rabbit 680RD, LICOR). Membranes were subjected to a second wash and were subsequently imaged using a LICOR Odyssey Imager and quantified using the LI-COR Image Studio v2.0.

Flow Cytometry—BMECs or day 14 EZ-sphere derived astrocytes and neurons were incubated with Accutase for 7 min. Cells were gently pipetted from the plate surface and were resuspended in their respective medium and counted on a hemocytometer. Cells were centrifuged for 5 min at 1000 g and fixed in 2% paraformaldehyde for 20 min at room temperature. Cells were then incubated in PBS supplemented with 40% goat serum and 0.1% Triton X-100 for 20 min at room temperature. Primary antibodies (Table 1) and control mouse or rabbit IgG at matching concentration were diluted in PBS supplemented with 40% goat serum for 30 min. Following primary antibody incubation, cells were washed three times in PBS containing 1% FBS. Alexa-488 goat anti-rabbit or anti-mouse IgG was added to the cells at a dilution of 1:200 in PBS containing 40% goat serum and incubated for 30 min. Cells were washed three times in PBS supplemented with 0.1% BSA and analyzed using a FACScaliber™ (BD).

P-Glycoprotein Efflux Transporter Activity—For transporter assays, iPSC-BMECs were sub-cultured onto Transwells at a density of 1 million cells/cm$^2$ and were maintained in monoculture or co-culture for 48 h in EC medium. Rhodamine 1,2,3 (10 μM, Sigma) was utilized as a PGP substrate and cyclosporine A (10 μM, CsA; Sigma) served as a PGP inhibitor. iPSC-BMECs were removed from co-culture conditions for 1 h to conduct Rhodamine 1,2,3 transport studies; no change in TEER was observed. BMECs were pre-incubated with CsA for 1 h at 37° C. on a rotating platform. The upper chamber received rhodamine 1,2,3 with or without CsA for 1 h at 37° C. on the rotating platform. Following incubation, aliquots were taken from the bottom chamber and fluorescence was quantified on a fluorescent plate reader and normalized to protein content quantified by BCA assay.

Permeability Measurements—Sodium fluorescein (10 μM, 376 Daltons; Sigma) was utilized to determine the permeability of the iPSC-BMEC barrier. Following 48 h of monoculture or co-culture, fresh EC medium was added to the Transwell system, with EC medium containing sodium fluorescein added to the top chamber and EC medium lacking sodium fluorescein added to the bottom chamber. 150 uL aliquots were taken from the bottom chamber at 0, 15, 30, 45, and 60 min, and immediately replaced with pre-warmed EC medium. Permeability coefficients were calculated based on the cleared volume of fluorescein from the top chamber to the bottom chamber.

Statistical Analysis—Data throughout the manuscript are presented as mean±SD. SigmaStat™ 3.0 software (Systat Software) was used for statistical analyses. Statistical comparisons were performed using one-way analysis of variance (ANOVA) with Holm-Sidak correction for multiple testing over all comparisons or unpaired Students t-test as appropriate. The statistical tests used for each particular data set are described in the description of the drawings.

Results

Figures 7A, 7B:
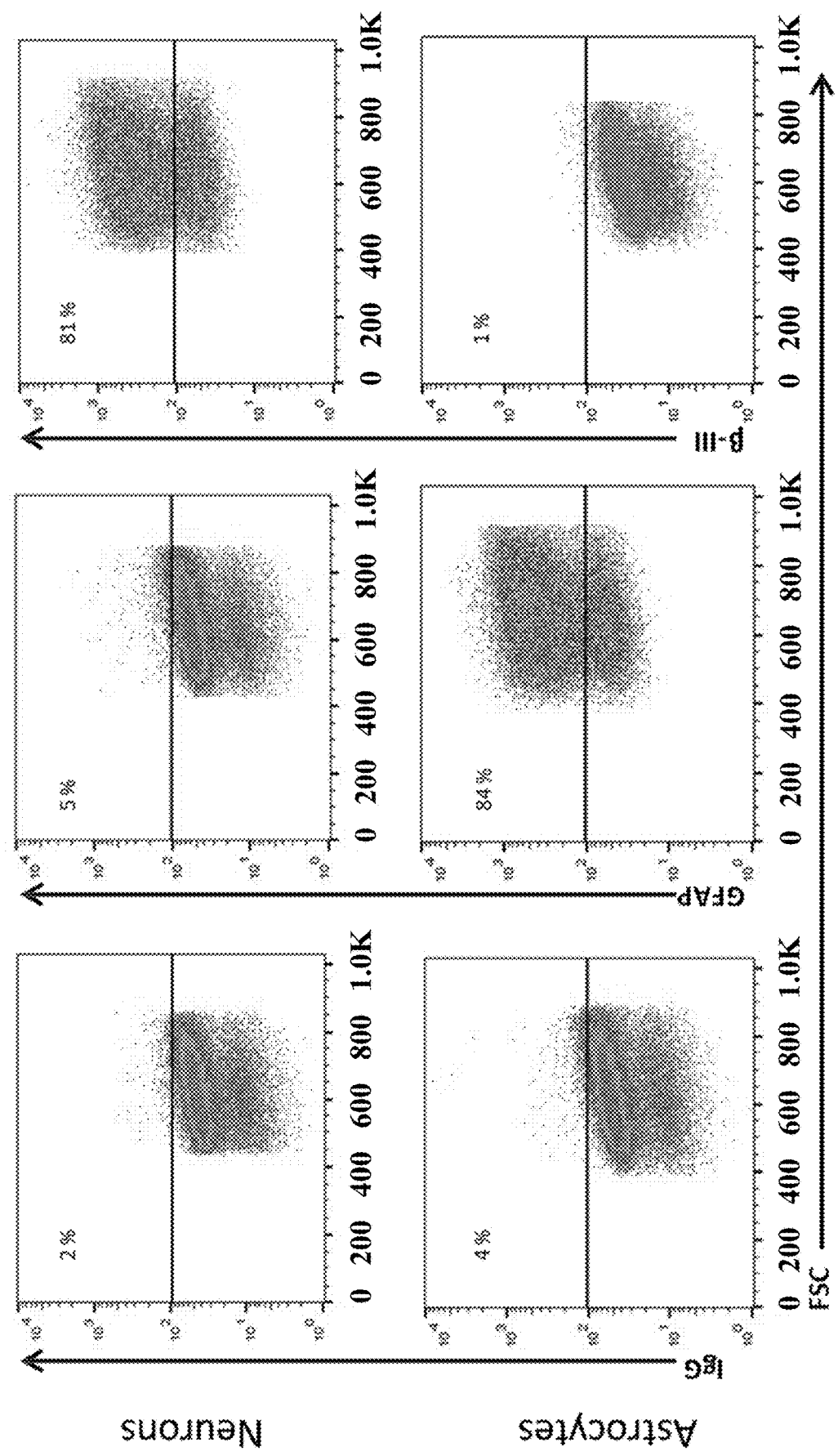
FIGS. 7A-7B show characterization of Day 14 EZ-sphere-derived astrocytes and neurons. (A) Representative flow cytometry density plots from EZ-sphere-derived astrocytes and neurons. Gates were drawn based on rabbit IgG control antibody labeling, and the percentage of total events having immunolabeling above rabbit IgG control is noted. 84% of the differentiated astrocyte population expressed GFAP. 81% of the differentiated neuron population expressed β-III tubulin. (B) CS03n2 EZ-sphere derived neurons and astrocytes continued to express β-III tubulin and GFAP, respectively following 48 h co-culture with CS03n2 iPSC-derived BMECs. Scale bars=100 µm.
Figures 7A, 7B:
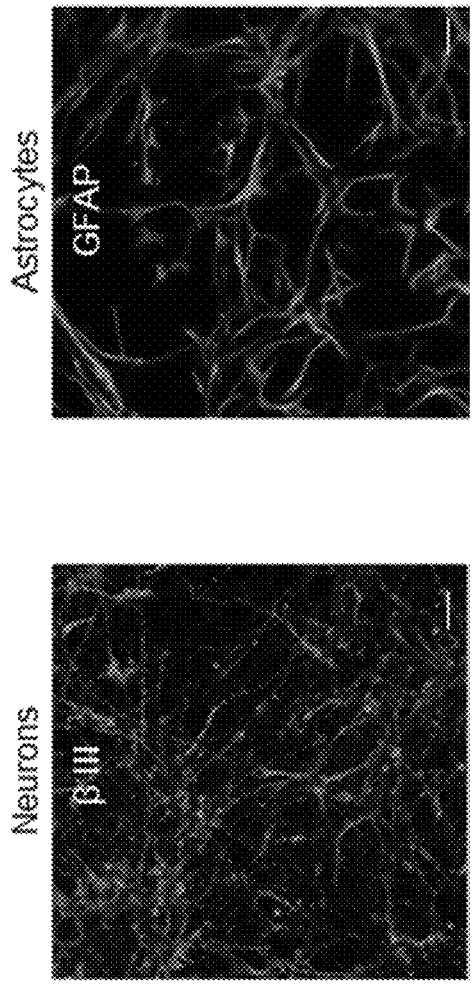
Figure 8:
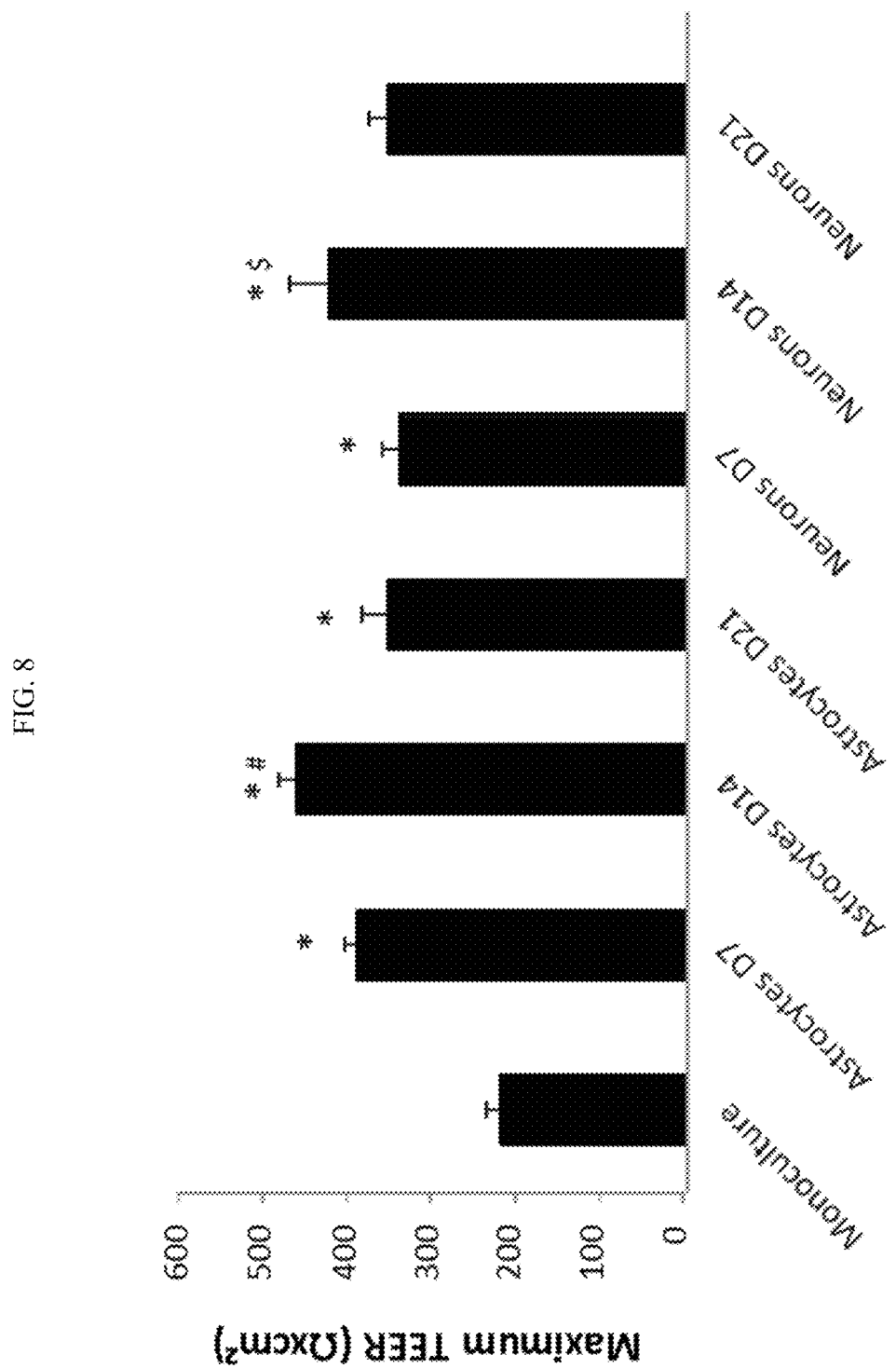
FIG. 8 depicts duration of neuron and astrocyte differentiation that induces maximum barrier tightening. 4.2 EZ-sphere-derived astrocytes and neurons were differentiated for 7 days, 14 days, and 21 days and combined in co-culture with IMR90-4-derived BMECs. TEER measurements were taken at 48 h after the initiation of co-culture. Statistical significance was calculated using ANOVA. *$p<0.05$ vs. monoculture, #$p<0.05$ vs. astrocytes D7 or D21, $$p<0.05$ vs. neurons D7 or D21. Values are mean±SD of three replicates from a single isolation/differentiation, and experiments were repeated for three more additional differentiations for verification of reported statistical trends.
Figures 9A, 9B:
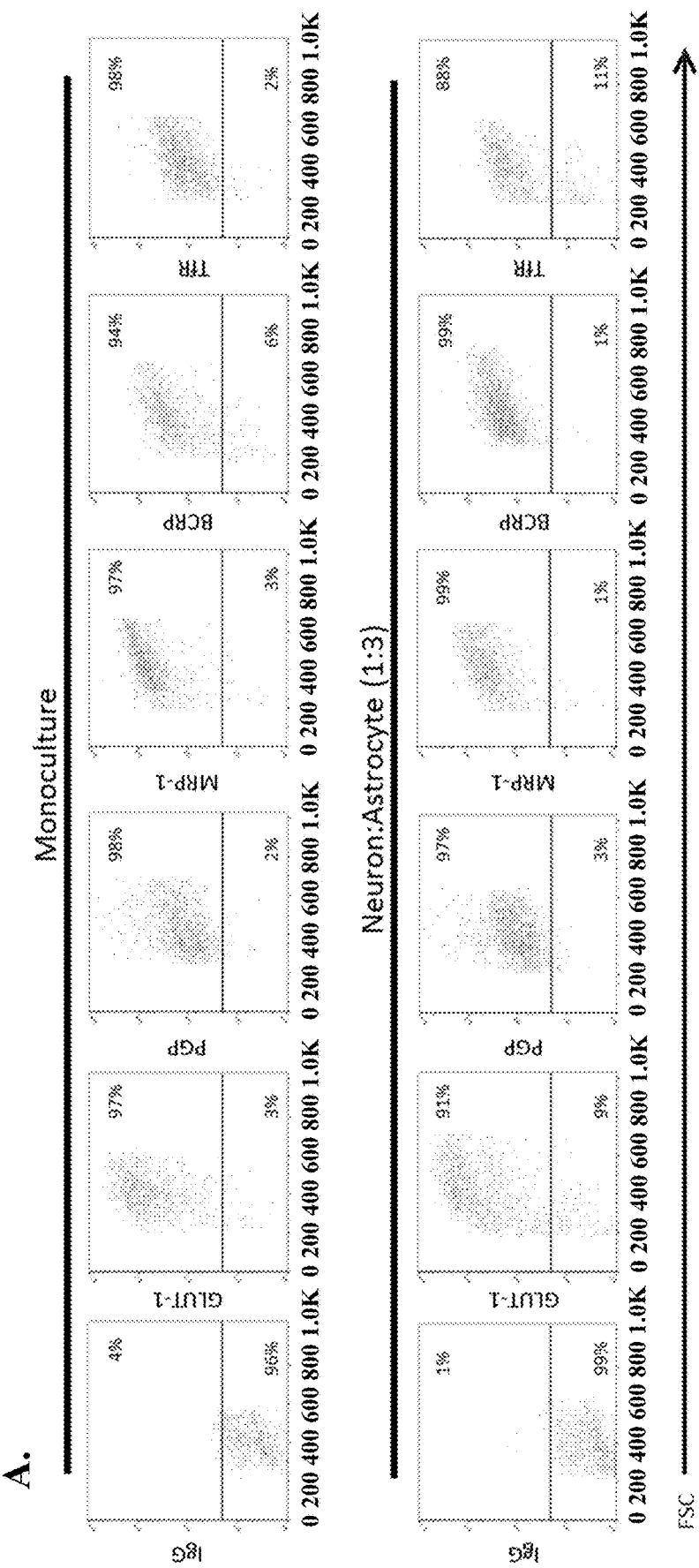
FIGS. 9A-9B show flow cytometric analysis of BMECs following co-culture with EZ-sphere-derived neurons and astrocytes (1:3). (A) Representative flow cytometry dot plots from IMR90-4 BMECs in monoculture or after 48 hours of co-culture with 4.2 EZ sphere-derived neuron and astrocytes (1:3). Gates were drawn based on mouse IgG negative control antibody immunolabeling, and the percentage of transporter immunopositive cells is noted in the insets to panel (A) and is compiled in panel (B). Geometric means of the transporter immunopositive populations were extracted from these flow data and are quantitatively compared in FIG. 5C. Statistical significance was determined using a Student's t-test. Values are mean±SD of three independent differentiations.
Figures 9A, 9B:
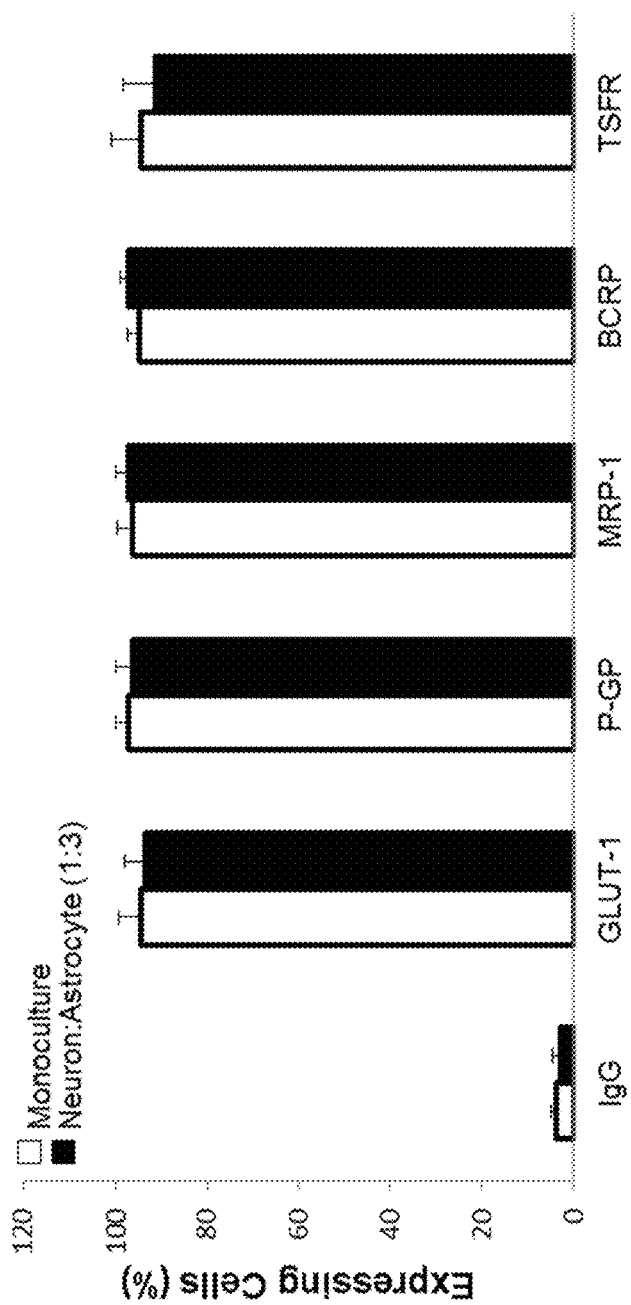
Figure 10:
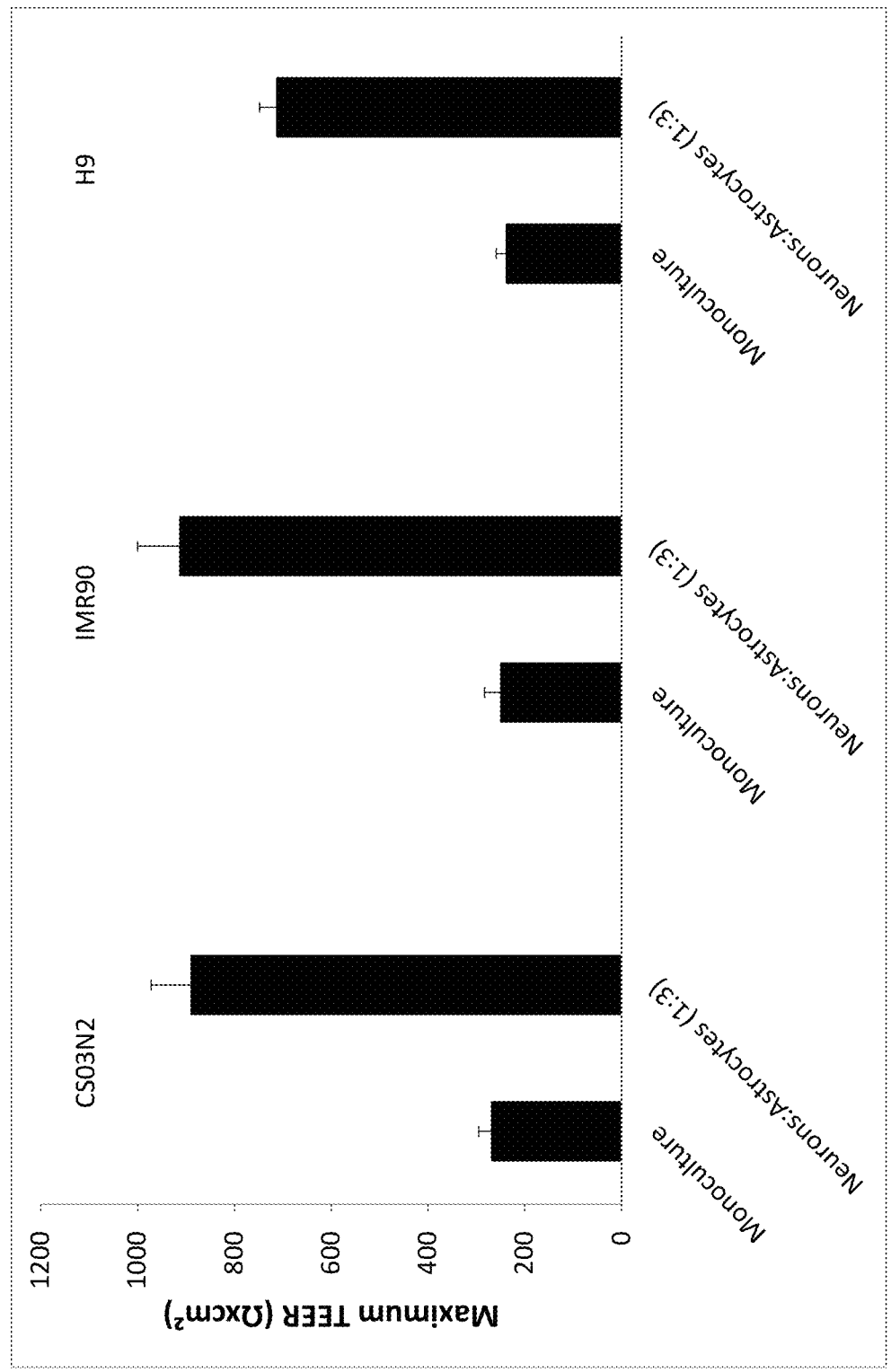
FIG. 10 shows development of multiple isogenic BBB models. BMECs, Neurons, and Astrocytes were derived from CSO3n2, IMR90, and H9 pluripotent stem cells. All three lines demonstrated that BMECs in co-culture with neurons:astrocytes (1:3) had enhanced barrier tightening.

Derivation of EZ-Sphere Derived Astrocytes and Neurons—Established protocols were used to differentiate astrocytes and neurons from EZ-spheres in a timely and efficient manner (Ebert et al. 2013, Sareen et al. 2014) (FIG. 1A). EZ-spheres were maintained in DMEM F/12 supplemented with bFGF and EGF (EZ Sphere Medium) and were mechanically dissociated weekly. EZ spheres were selectively differentiated toward a neuronal population by culture in DMEM/F12 supplemented with B27 (w/o vitamin A) (Neuron Induction Medium) (FIG. 1A). EZ-sphere-derived neurons expressed βIII tubulin, a neuron-specific marker, while astrocyte markers, GFAP, an intermediate filament protein expressed by astrocytes, and S100 calcium binding protein (S100B), a mature glial-specific marker, were completely absent in this population. EZ-sphere-derived neurons were also negative for paired box protein 6 (PAX-6), an early ectoderm marker. EZ-spheres were also differentiated to astrospheres, a neural progenitor population, by Astrocyte Induction Medium supplemented with retinoic acid. Astrospheres were then further differentiated to astrocytes in DMEM/F12 supplemented with N2 (Astrocyte Induction Medium), leading to cell populations exhibiting glial morphology and expressing GFAP and S100B. Further confirming the selective differentiation to the astrocyte lineage, the EZ-sphere derived astrocytes did not express PAX-6 or βIII tubulin. Flow cytometry indicated that 80±7% of astrocytes and 82±9% of neurons expressed GFAP and βIII tubulin, respectively (FIGS. 7A-7B). Astrocytes and neurons differentiated from EZ-spheres for 7, 14, and 21 days were investigated for their capacity to induce barrier properties in iPSC-derived BMECs. Day 14 astrocytes and neurons provided the greatest TEER elevation and were therefore employed for subsequent experiments (FIG. 8). In addition, astrocytes and neurons continued to express βIII tubulin and GFAP, respectively, following co-culture with iPSC-derived BMECs (FIGS. 7A-7B). Taken together, iPSC-sourced EZ-spheres generated populations of BBB-inducing astrocytes or neurons in a relatively short 14-day timeframe.

Figure 2A:
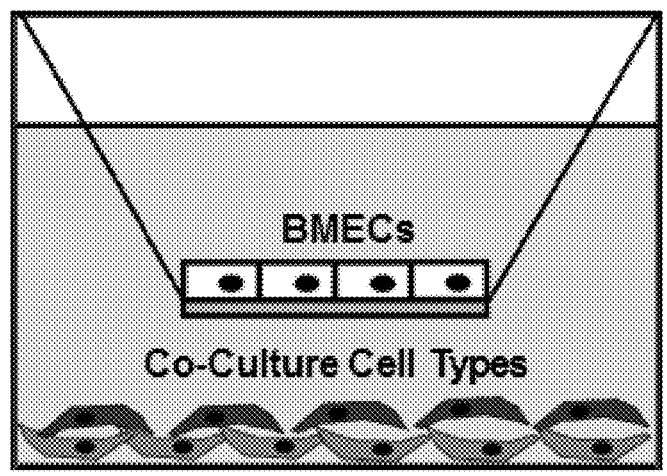
FIGS. 2A-2B depict determination of the BBB inductive effects of EZ-sphere-derived astrocytes and neurons. (A) Co-culture was conducted using a Transwell system. BMECs were seeded on the Transwell filter with co-cultured cell types seeded at the bottom of the well. (B) Primary rat BMECs were co-cultured with iPSC 4.2 EZ-sphere-derived neurons, astrocytes or a mixture of neurons and astrocytes (1 neuron: 3 astrocytes) and TEER was monitored. Statistical significance was calculated using ANOVA.*$p<0.05$ vs. rat BMECs; #$p<0.05$ vs. neurons. Values are mean±SD of three replicates from a single rat BMEC isolation and a single neuron and astrocyte differentiation, and experiments were repeated for two additional independent isolations and differentiations for verification of reported statistical trends.
Figure 2B:
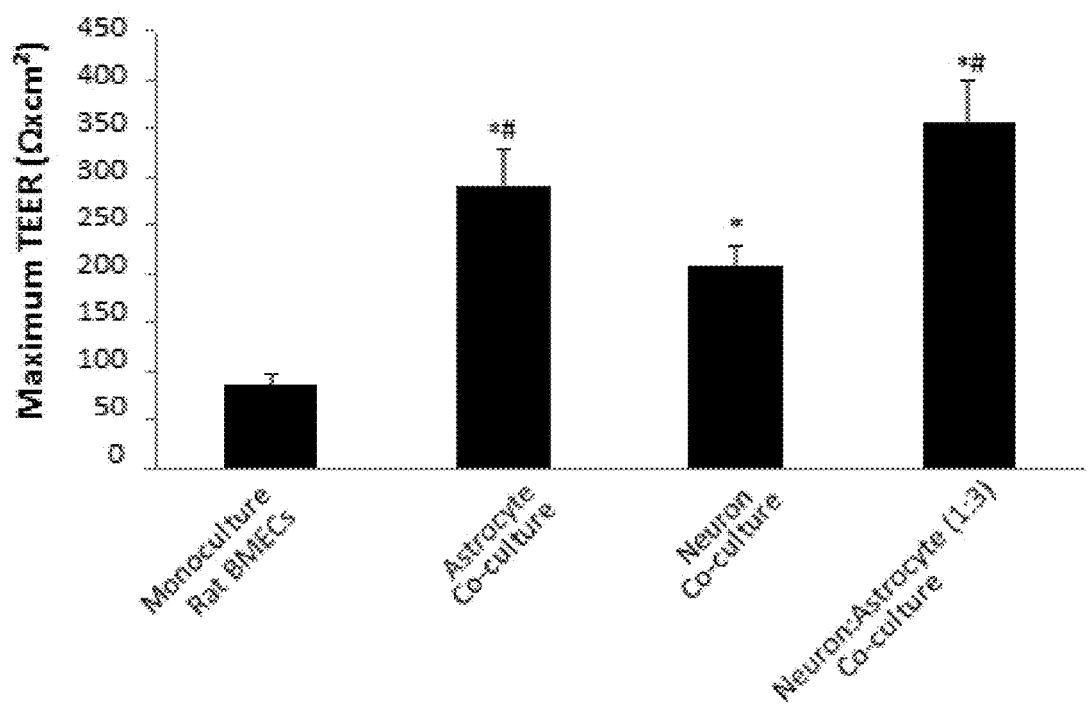

Co-Culture of BMECs with EZ-Sphere-Derived Astrocytes and Neurons Enhances Barrier Tightness—Next, iPSC-derived BMECs were co-cultured with EZ-sphere-derived astrocytes and neurons. As described previously, iPSC-derived BMECs express key BBB markers including the endothelial cell marker Pecam, the BBB glucose transporter Glut-1, tight junction proteins, occludin and claudin-5, and the efflux transporter PGP (Lippmann et al. 2012) (FIG. 1B). The effects of co-culturing EZ-sphere-derived astrocytes and neurons on barrier formation in purified BMECs were evaluated as outlined in FIG. 1C. Importantly, these co-cultures required identification of a common medium suitable for all cell types present. To identify a suitable co-culture medium, iPSC-derived BMECs and co-culture cell types (astrocytes and/or neurons) were differentiated in parallel and placed in co-culture in several media (see Materials and Methods) containing varying amounts of PDS and FBS on day 8 of the BMEC differentiation (FIG. 1C). The greatest barrier induction was observed in EC medium containing 1% PDS and 20 ng/mL bFGF (EC+bFGF/+PDS) for the initial 24 h of co-culture (days 8-9), followed by a switch to EC medium containing 1% PDS but lacking bFGF (EC –bFGF/+PDS) for days 9-12, as previously described (Lippmann et al. 2014). To demonstrate that EZ-sphere-derived neurons and astrocytes were capable of inducing BBB properties, they were first co-cultured with primary rat BMECs and barrier formation monitored by TEER (FIG. 2A). Monocultured rat BMECs had a TEER value of 86±11 Ω×cm$^2$, and when in co-culture with EZ-sphere derived astrocytes the rat BMEC TEER rose to 291±38 Ω×cm$^2$ ($p<0.05$). Similarly, co-culture with EZ-sphere-derived neurons elevated the rat BMEC TEER to 208±21 Ω×cm$^2$ ($p<0.05$). A combination of EZ-sphere-derived neurons and astrocytes (1:3) elevated TEER of rat BMECs to 356±42 Ω×cm$^2$ ($p<0.05$) (FIG. 2B). Thus, EZ-sphere-derived neural cells are capable of inducing barrier function in primary rat BMECs.

Figures 3A, 3B, 3C:
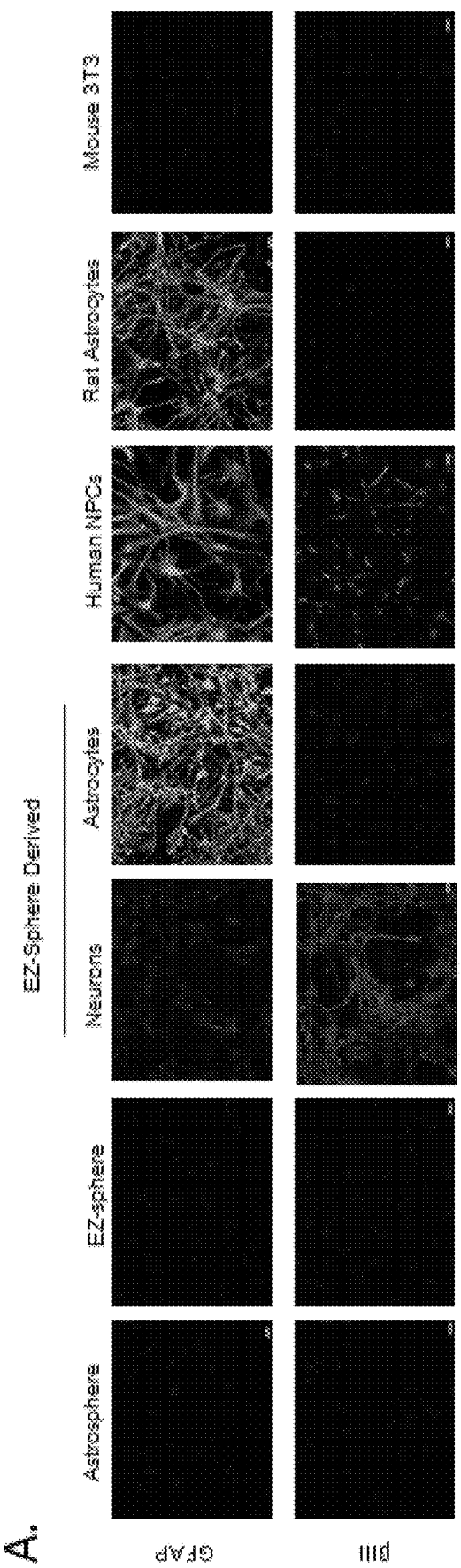
FIGS. 3A-3C show optimization of co-culture conditions to induce barrier tightening in iPSC-derived BMECs. A variety of co-cultured cells were examined for their capacity to induce barrier tightening in IMR90-4 iPSC-derived BMECs. (A) Immunocytochemical probing for GFAP and β-tubulin III was utilized to examine the distribution of astrocytes and neurons, respectively. Astrospheres, EZ-spheres and EZ-sphere-derived astrocytes and neurons were generated from the iPSC 4.2 EZ-spheres. Primary human NPC-derived mixtures of astrocytes and neurons, primary rat astrocytes and mouse 3T3 fibroblasts were employed as comparative controls. Scale bars=200 µm. (B) Maximum TEER values were reached 48 h after the initiation of co-culture (Day 10). All co-cultured cells were seeded at 25,000 cells/cm$^2$. EZ-sphere-derived neural cells were employed as either pure neuron or astrocyte cultures, or as mixtures as denoted. (C) Fluorescein permeability was measured 48 h following the initiation of co-culture (Day 10). Statistical significance was calculated using ANOVA. *$p<0.05$ vs. monoculture, $^{\$}p<0.05$ vs. neuron or astrocyte co-culture, #$p<0.05$ vs. all groups. Values are mean±SD of three replicates from a single isolation/differentiation, and experiments were repeated for three additional differentiations for verification of reported statistical trends.
Figures 3A, 3B, 3C:
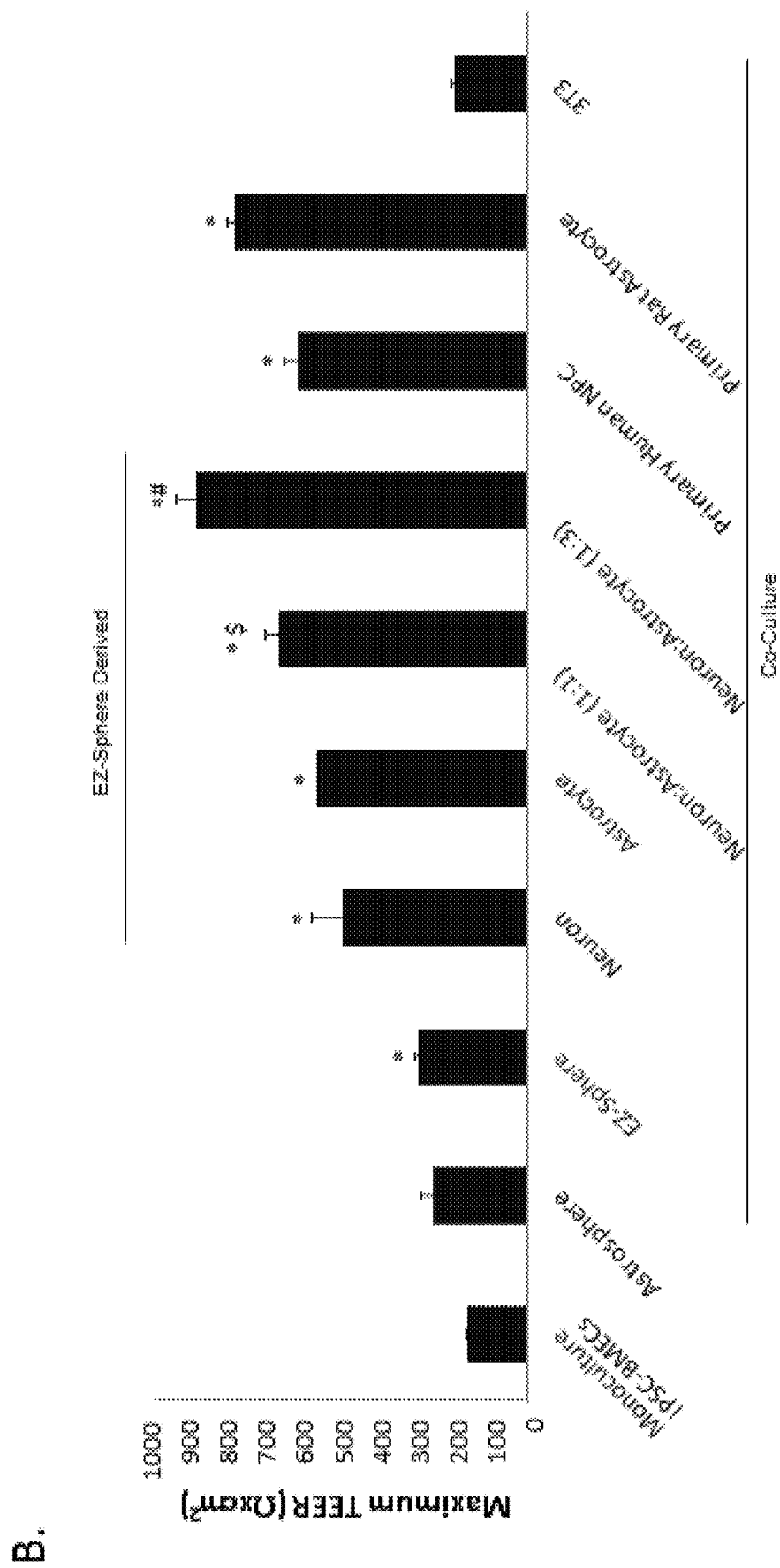
Figures 3A, 3B, 3C:
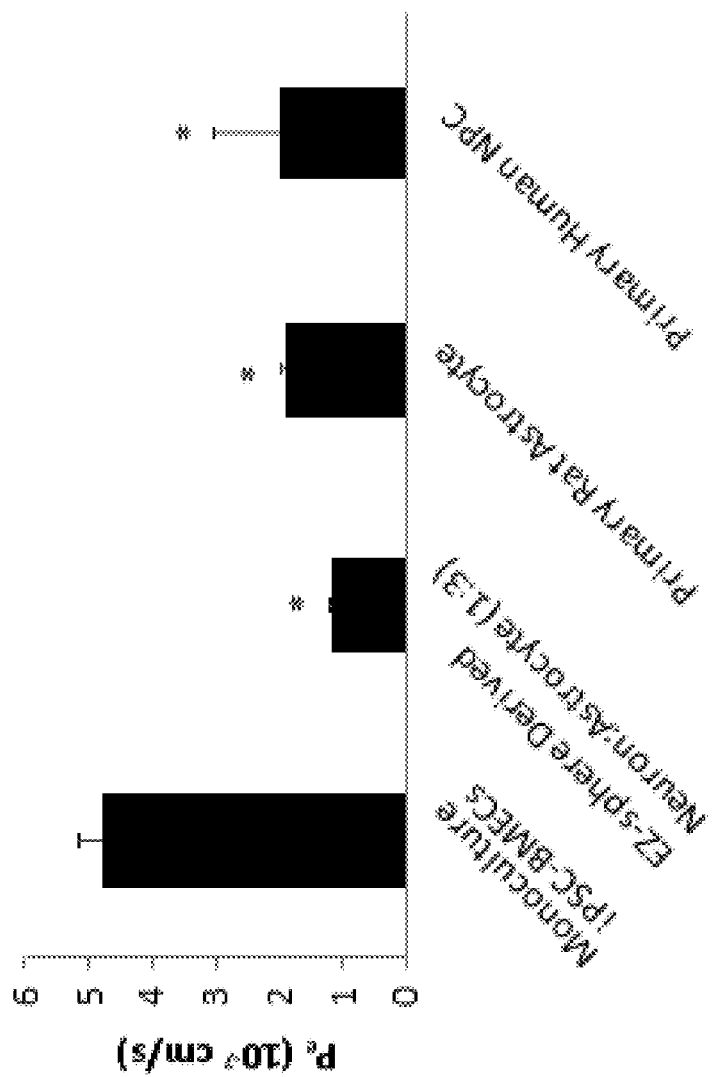

Since EZ-sphere-derived neural cells induced barrier properties in primary rat BMECs, the effects of EZ-sphere derived astrocytes and neurons on TEER in co-culture models with human iPSC-derived BMECs was systematically examined by comparison with several other inductive and non-inductive cell types (FIGS. 3A and 3B). Co-culture with EZ-sphere-derived neurons and astrocytes significantly elevated the TEER of iPSC-derived BMECs compared with monoculture (neuron 491±86 Ω×cm$^2$ ($p<0.05$); astrocyte 558±4 Ω×cm$^2$ ($p<0.05$); vs. monoculture 153±9 Ω×cm$^2$). Combining EZ-sphere-derived neurons and astrocytes further elevated the TEER compared to co-culture with either astrocytes or neurons alone. A 1:1 ratio of neurons to astrocytes boosted TEER of co-cultured BMECS to 661±41 Ω×cm$^2$ ($p<0.05$) while a 1:3 ratio of neurons to astrocytes further elevated TEER to 886±54 Ω×cm$^2$ ($p<0.05$).

By comparison, primary human neural progenitor cell (NPC)-derived mixtures of astrocytes and neurons (FIG. 3A) raised TEER values of co-cultured iPSC-derived BMECs to 611±40 Ω×cm$^2$ ($p<0.05$) (FIG. 3B), a similar value as previously reported (Lippmann et al. 2012). Co-culture with primary rat astrocytes also elevated the iPSC- BMEC TEER (784±19 Ω×cm² (p<0.05)) as previously demonstrated (Lippmann et al. 2014). To assess whether the EZ-sphere neural progenitors affected BMEC TEER, we co-cultured undifferentiated EZ spheres with iPSC-derived BMECs. EZ-spheres and EZ-sphere derived astrospheres that did not yet express astrocyte or neuronal markers (FIG. 3A) only modestly elevated TEER compared to monocultured iPSC-derived BMECs (247±33 Ω×cm² (N.S.); 285±12 Ω×cm² (p<0.05), respectively). Finally, mouse 3T3 fibroblasts were used as a non-inductive co-culture control. 3T3 cell co-culture did not elevate TEER with statistical significance (187±14 Ω×cm² (N.S.)) above monocultured BMECs.

We also utilized fluorescein permeability to assess effects of EZ-sphere-derived cells on iPSC-derived BMEC barrier properties (FIG. 3C). Monocultured iPSC-derived BMECs exhibited a sodium fluorescein permeability of $P_e=4.8±0.3×10^{-7}$ cm/s. Co-culture with EZ-sphere-derived neurons and astrocytes (1:3) resulted in significantly reduced $P_e$ of $1.20±0.01×10^{-7}$ cm/s (p<0.05), consistent with the elevated co-culture TEER. Similarly, NPC-derived astrocytes and neurons and primary rat astrocytes significantly reduced fluorescein permeability, indicating a BMEC barrier tightening (NPC-derived neural cells $P_e=2.0±1.0×10^{-7}$ cm/s (p<0.05), primary rat astrocytes $P_e=1.9±0.1×10^{-7}$ cm/s (p<0.05); respectively). EZ-sphere derived neurons and astrocytes, specifically at a ratio of 1:3, enhanced barrier tightening in BMECs and benchmarked similarly to other non-stem cell-derived human NPCs and rat astrocytes.

Figures 4A, 4B, 4C, 4D, 4E:
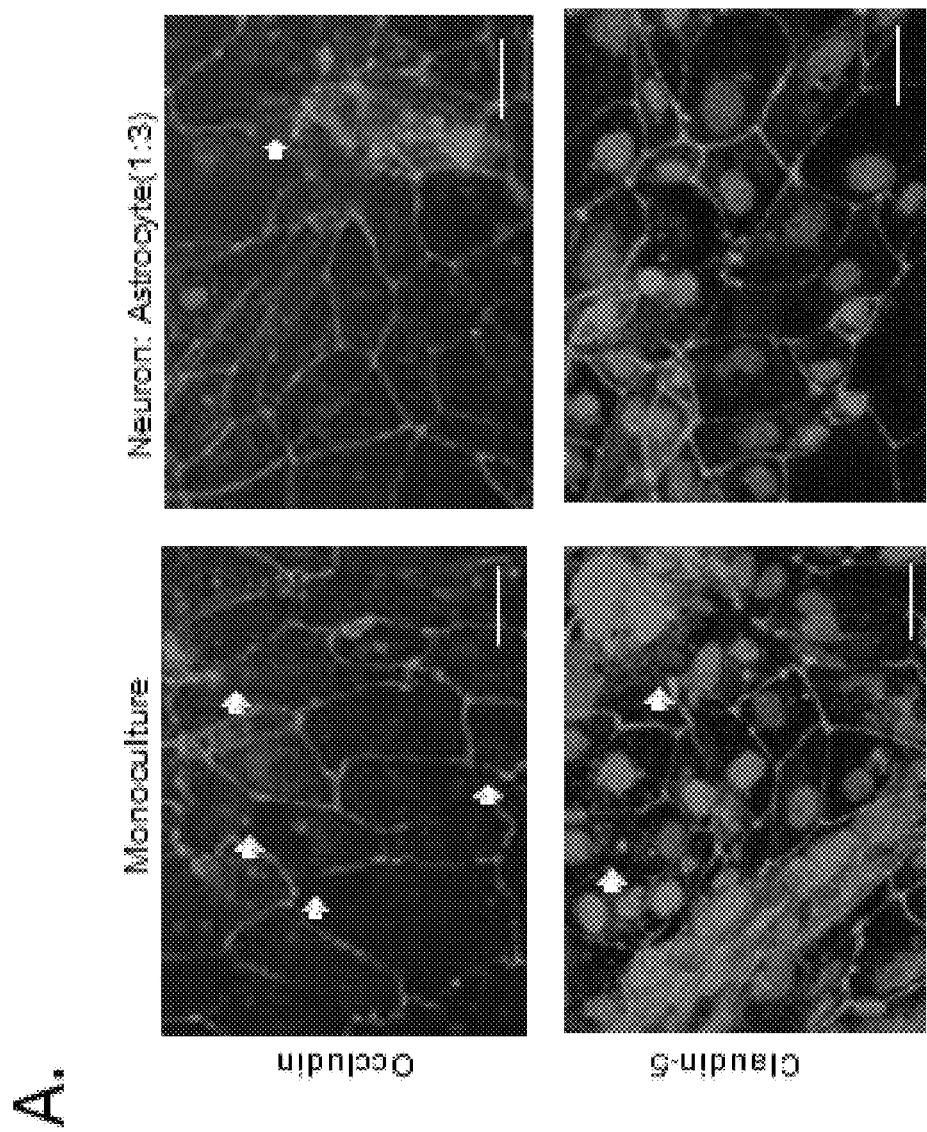
FIGS. 4A-4E show analysis of tight junction continuity following EZ-sphere co-culture. Tight junction protein localization and expression levels were investigated in IMR90-4 iPSC-derived BMECs following 48 h of co-culture with iPSC 4.2 EZ-sphere-derived neurons and astrocytes (1:3). (A) Immunocytochemistry of occludin and claudin-5 revealed discontinuous tight junctions (white arrows). Scale bars=50 µm. (B) Discontinuous junctions were quantified in BMECs in monoculture and co-culture conditions by counting cells that contained at least one discontinuous tight junction. (C) Additional quantification of tight junction localization in BMECs in monoculture and co-culture conditions was conducted by calculating the area of each image having occludin and claudin-5 immunoreactivity, resulting in the area fraction index. The data is normalized to monoculture conditions and expressed as a percentage. Statistical significance for panels (B) and (C) was calculated using a Student's t-test. *$p<0.05$ vs. monoculture. Values are mean±SD of three blinded independent differentiations. (D) Western blot of tight junction proteins occludin and claudin-5 in both monoculture and co-culture conditions with a β-actin loading control. A single lane representative of triplicate Western blot samples is shown. (E) Quantification of Western blots to compare tight junction protein expression levels. Co-culture samples were independently normalized to each respective monoculture sample. Statistical significance was calculated using a Student's t-test. Values are mean±SD of three independent differentiations.

Co-Culture Increases Tight Junction Localization in BMECs—To determine whether the enhanced iPSC-derived barrier properties upon co-culture with EZ-sphere-derived cells were related to structural changes in tight junctions, the localization and continuity of tight junction proteins were examined by immunocytochemistry. iPSC-derived BMECs in monoculture displayed junctions that were frequently discontinuous for occludin and claudin-5 (FIG. 4A). Following 48 h of co-culture with EZ-sphere-derived neurons and astrocytes (1:3), the number of cells with discontinuous junctions decreased substantially (FIGS. 4A and 4B), corresponding to an overall increase in junctional occludin and claudin-5 immunoreactivity (FIG. 4C, 83±24% increase in occludin and 44±14% increase in claudin-5 area fraction indices compared to monoculture (p<0.05)). In addition, Western blotting was used to evaluate if co-culture affected tight junction protein expression levels (FIG. 4D). Co-culture with EZ-sphere derived neurons and astrocytes resulted in a slight, statistically insignificant increase in occludin and claudin-5 levels compared to monoculture (FIG. 4E). Taken together these results indicate that co-culture with EZ-sphere derived astrocytes and neurons enhances barrier properties in iPSC-derived BMECs, and suggest that these changes in barrier properties result from improved formation and maintenance of tight junctions.

Figures 5A, 5B, 5C:
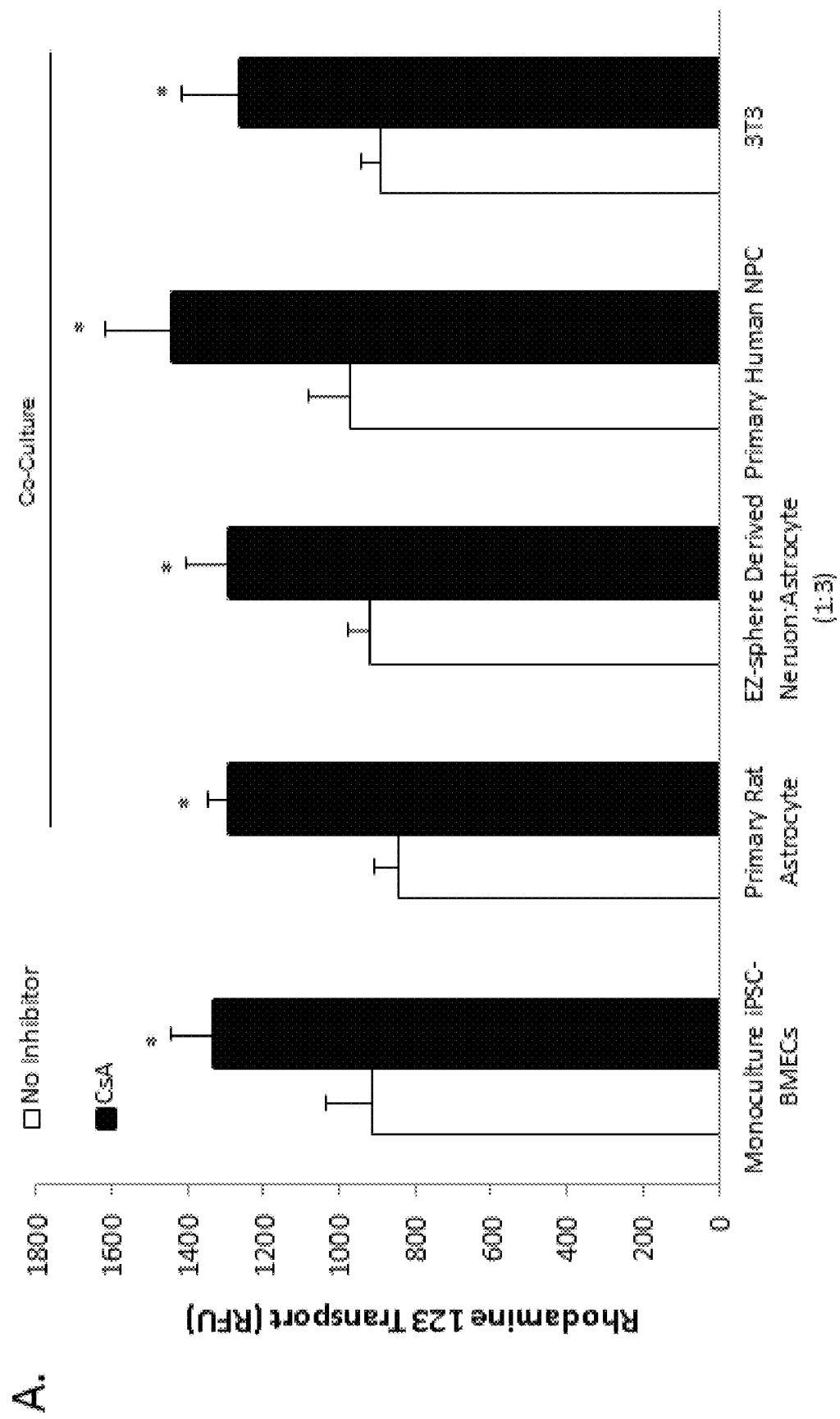
FIGS. 5A-5C show evaluation of BMECs following co-culture. (A) To assess active efflux transporter activity in IMR90-4 iPSC-derived BMECs, the trans-BMEC transport of PGP substrate rhodamine 123, with and without the PGP inhibitor cyclosporine A (CsA) was measured. IMR90-4 iPSC-derived BMECs were co-cultured with rat astrocytes, human NPC-derived astrocytes and neurons, iPSC 4.2 EZ-sphere-derived neurons and astrocytes (1:3), or mouse 3T3 fibroblasts. Rhodamine 123 transport from the apical to the basolateral chamber was measured in the two-compartment co-culture model in the presence or absence of CsA and reported as raw fluorescence units (RFU). Statistical significance was calculated using ANOVA.*$p<0.05$ vs. no inhibition control for each experimental condition. Values are mean±SD of three replicates from a single differentiation/isolation, and experiments were repeated for two more additional independent differentiations to confirm statistical trends. (B) Immunocytochemistry analysis of IMR90-4 iPSC-derived BMECs in mono-culture or after 48 hours of co-culture with 4.2 iPSC EZ-sphere-derived neurons and astrocytes (1:3) probing for glucose transporter, Glut-1, efflux transporters, p-glycoprotein (PGP), multi-drug resistance associated protein 1 (MRP-1), breast cancer resistance protein (BCRP), or transferrin receptor, TfR, expression. Scale bar=100 µm. (C) Quantitative transporter expression levels were determined using flow cytometry. Geometric means of positively immunolabeled cell populations were used to compare expression levels with and without co-culture. Sample flow cytometry data is shown in FIGS. 9A-9B. The data are normalized to monoculture expression levels. Statistical significance was determined using a Student's t-test. Values are mean±SD of three independent differentiations.
Figures 5A, 5B, 5C:
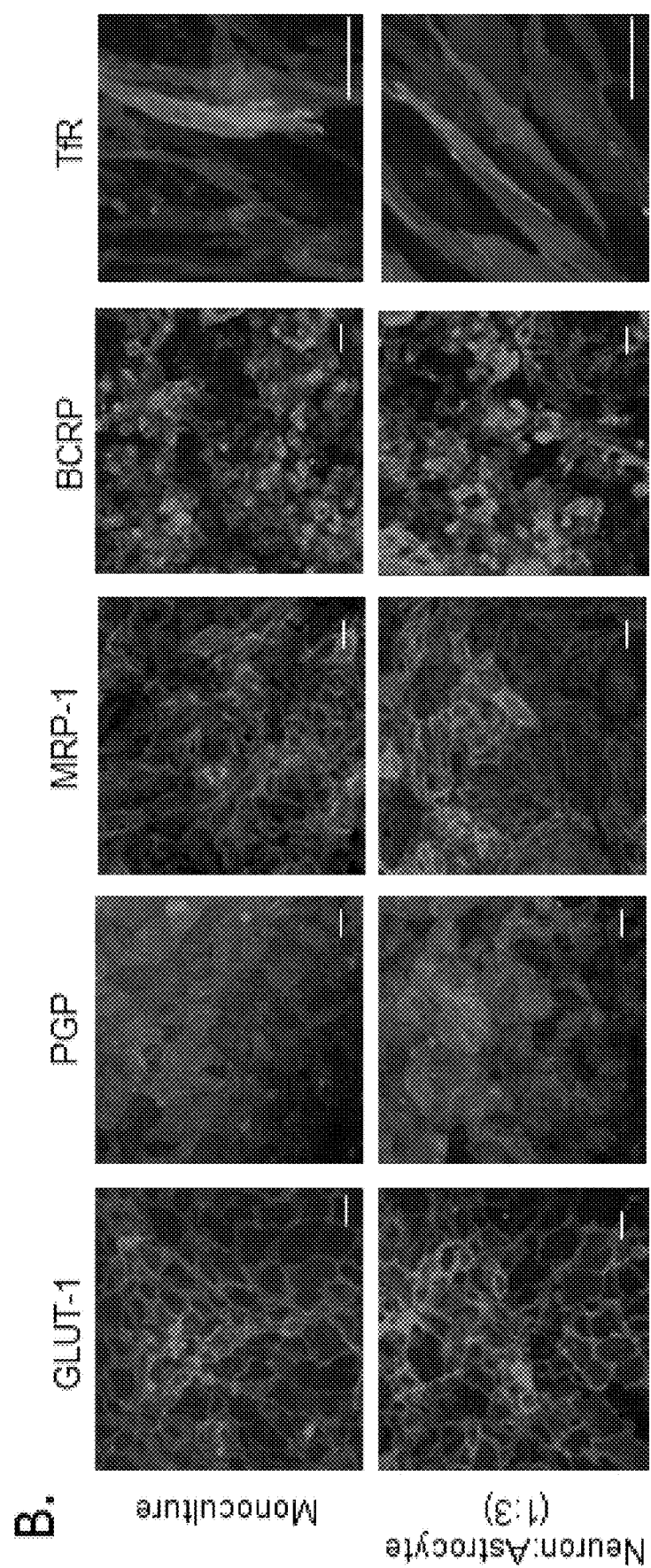
Figures 5A, 5B, 5C:
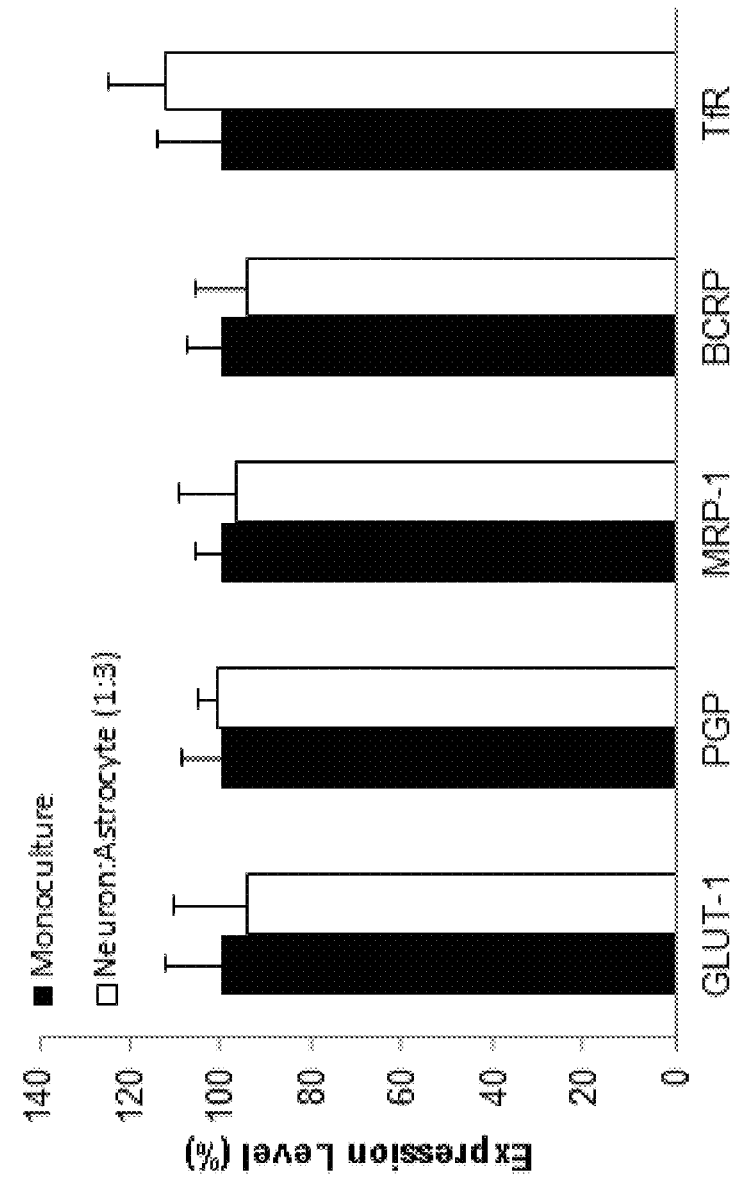

BMEC Transporters are Unchanged by Co-Culture—The effects of EZ-sphere-derived cell co-culture on PGP efflux transporter activity in iPSC-derived BMECs were investigated by measuring the transport of rhodamine 123 across the iPSC-derived BMEC monolayer. PGP activity was compared between iPSC-derived BMECs in monoculture and iPSC-derived BMECs in co-culture with EZ-sphere-derived neurons and astrocytes (1:3). BMECs in monoculture exhibited increased transport of rhodamine 123 following cyclosporine A (CsA) inhibition (45±8% (p<0.05), indicative of the baseline PGP activity in iPSC-derived BMECs (FIG. 5A). After co-culture with EZ-sphere derived neurons and astrocytes, PGP activity was statistically indistinguishable from monocultured iPSC-derived BMECs (40±8% increase in presence of CsA). For comparison, iPSC-derived BMECs in co-culture with primary rat astrocytes, NPC-derived astrocytes and neurons or mouse 3T3 fibroblasts also yielded statistically indistinguishable PGP activities versus iPSC-derived BMEC monocultures. Taken together, these results indicate that PGP is active in the iPSC-derived BMECs as previously described and that co-culture with iPSC-derived or primary-derived astrocytes and neurons does not affect this activity (Lippmann et al. 2012, Lippmann et al. 2014, Wilson et al. 2015). Additionally, co-culture with EZ-sphere derived neurons and astrocytes (1:3) did not affect the localization or expression levels of Glut-1, PGP, MRP-1, BCRP, or the transferrin receptor, TfR (FIGS. 5B, 5C, 9A, 9B). Thus, barrier tightening remains the dominant phenotypic effect of co-culturing iPSC-derived BMECs with EZ-sphere derived neurons and astrocytes.

Figures 6A, 6B, 6C, 6D, 6E:
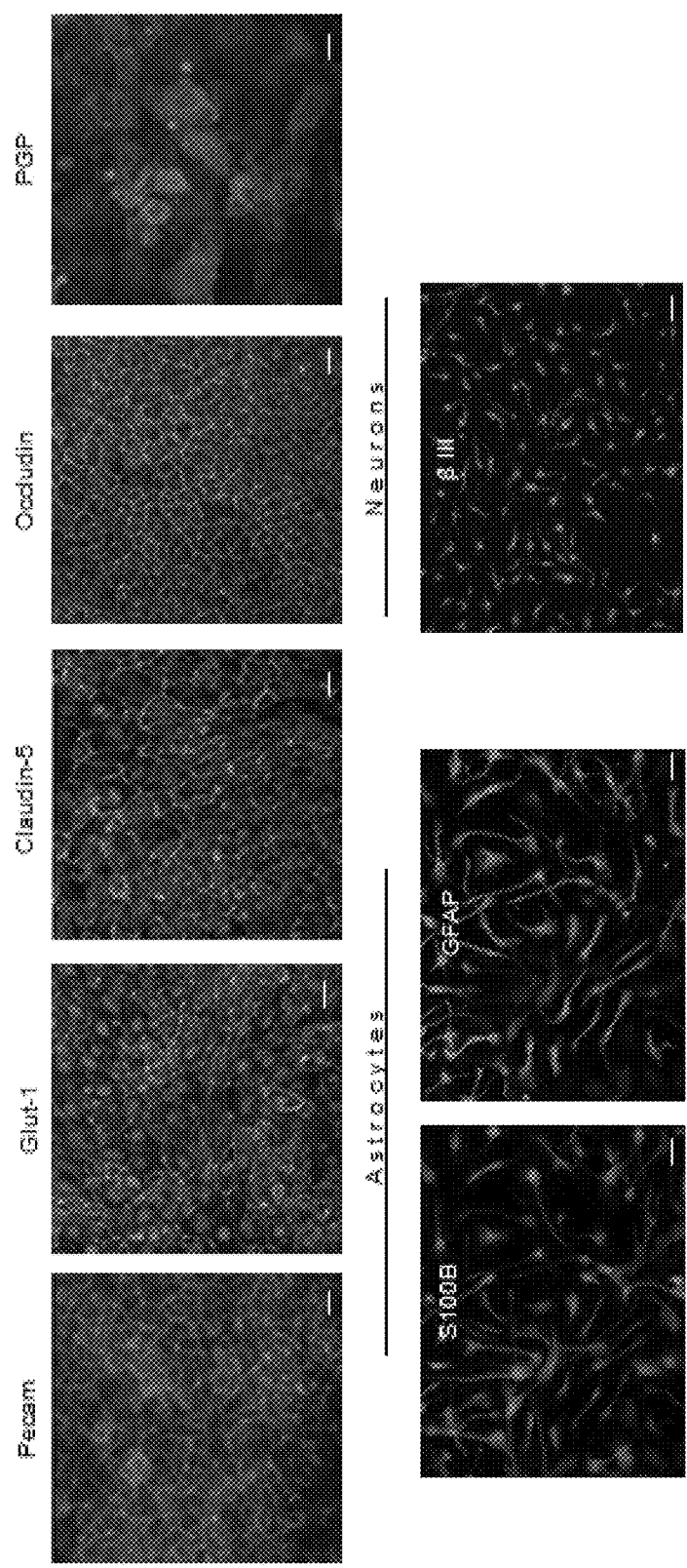
FIGS. 6A-6E show development of an isogenic neurovascular unit. iPSC-derived BMECs and EZ-sphere-derived astrocytes and neurons were differentiated from the same CSO3n2 iPSC line. (A) Immunocytochemical analysis of BBB markers in CSO3n2-derived BMECs. Scale bar=100 µm. (B) Immunocytochemical of astrocyte and neuron markers in astrocytes and neurons differentiated from CSO3n2 EZ-spheres. Scale bars=100 µm. (C) Temporal TEER profile for CSO3n2 iPSC-derived BMECs with and without co-culture with CS03n2 iPSC-derived neurons and astrocytes. Statistical significance was calculated using Student's t-test. *$p<0.05$ vs. monoculture. Values are mean±SD of three replicates from a single differentiation, and experiments were repeated for two additional independent differentiations to verify statistical trends. (D) Sodium fluorescein permeability measured at 48 h after the initiation of co-culture. Statistical significance was calculated using Student's t-test. *$p<0.05$ vs. monoculture. Values are mean±SD of three replicates from a single differentiation, and experiments were repeated for two additional independent differentiations to verify statistical trends. (E) PGP efflux transporter activity was measured 48 h after initiation of co-culture. Statistical significance was calculated using ANOVA. *$p<0.05$ vs. no-inhibition. Values are mean±SD of three replicates from a single differentiation, and experiments were repeated for two additional independent differentiations to verify statistical trends.

Derivation of an Isogenic iPSC-Derived Human BBB Model—Having demonstrated the barrier-enhancing effects of EZ-sphere derived neurons and astrocytes on iPSC-derived BMECs, as indicated by an increase in TEER, reduced permeability, and a decrease in the discontinuous tight junctions, we next investigated the potential of deriving BMECs, astrocytes and neurons from the same donor-derived iPSC line (CSO3iCTRn2) to construct an isogenic model of the human NVU. As demonstrated for the IMR90-4 (BMECs) and 4.2-iPSC (astrocytes and neurons) lines above, CS03iCTRn2-derived BMECs, neurons, and astrocytes expressed the appropriate tissue-specific markers (FIGS. 6A and 6B). Co-culture of CS03iCTRn2-derived BMECs with neurons:astrocytes (1:3) enhanced TEER nearly 4-fold compared to monoculture (785±30 Ω×cm² vs. 201±14 Ω×cm²; respectively (p<0.05)), and this barrier was maintained at ~700 Ω×cm² for 5 days (FIG. 6C). Barrier tightening was also demonstrated in the isogenic co-culture model as a 13-fold decreased fluorescein permeability compare to monocultured CS03iCTRn2-derived BMECs. ($P_e=0.62±0.11×10^{-7}$ cm/s vs. $8.1±0.9×10^{-7}$ cm/s; respectively (p<0.05)) (FIG. 6D). PGP-efflux transporter activity in the isogenic model was unaffected by co-culture, with monoculture BMECs displaying a 38±14% increase in rhodamine 1,2,3 transport following CsA inhibition, while co-culture BMECs had a 45±12% increase in PGP efflux transporter activity (FIG. 6E). As with co-cultures derived from mixed iPSC lines (FIGS. 2-5), we successfully co-cultured BMECs with astrocytes and neurons derived from donor-matched iPSCs and observed enhanced barrier properties in the BMEC population.

Discussion

This study demonstrates that iPSC EZ-sphere-derived astrocytes and neurons can be combined with iPSC-derived BMECs to form a completely human iPSC-derived BBB model comprising these three key NVU cell types. Importantly, many models are chimeric in that they employ cells of the neurovascular unit from differing species. Often, the isolations of each cell type are distinct protocols using tissue from differently aged animals (Lippmann et al. 2013, Deli et al. 2005, Syvänen et al. 2009, Warren et al. 2009). Thus, the technical complexity of multicellular, BBB models can be appreciable. Using iPSC technology, it is possible to derive each human cell type from a single scalable, undifferentiated iPSC source. However, typical protocols for deriving iPSC neurons and astrocytes can take weeks to months to differentiate (Kim et al. 2011, Krencik & Zhang 2011), complicating the logistics of constructing an iPSC-based human BBB model. By contrast, EZ-spheres are a self-renewing pre-rosette neural stem cell population that can be cultured in suspension for prolonged periods of time, passaged via mechanical dissociation techniques, and differentiated to a range of neural lineages in a relatively short time (2 weeks). As demonstrated above, these two-week differentiated neuron and astrocyte populations are capable of substantially improving the barrier properties in iPSC-derived BMECs. Thus, combined with the relatively short BMEC differentiation (8 days), the ability to culture the EZ spheres in self-renewing "intermediate" stage prior to neuron and astrocyte differentiation greatly diminishes the logistical challenges in modeling the BBB with iPSC-derived cells.

The capability of EZ-sphere-derived astrocytes and neurons to enhance BBB properties was first confirmed by their ability to increase in barrier tightness in co-cultured rat BMECs. Subsequently, moving toward co-culture with iPSC-derived BMECs, it was found that EZ-sphere and astrosphere progenitors were not appreciably inductive. However, further differentiated EZ-sphere-derived astrocytes and neurons increased BMEC barrier properties, indicating that neural cell specification is key to BBB induction. Interestingly, we found that co-culture with EZ-sphere-derived astrocytes yielded enhanced barrier induction compared to co-culture with neurons, consistent with previous reports that astrocyte co-cultures were more inductive of BMEC barrier properties than neuronal co-cultures (Schiera et al. 2005). BMEC co-culture with a mixture of EZ-sphere-derived astrocytes and neurons yielded even greater improvements in barrier function than either cell type alone, and the most inductive 1:3 ratio of neurons to astrocytes closely resembles the reported distribution in the adult human brain (Azevedo et al. 2009, Herculano-Houzel & Lent 2005). In terms of absolute inductive capacity, the EZ-sphere derived astrocytes and neurons compared favorably with other co-culture models. Previously, we demonstrated that TEER is elevated in iPSC-derived BMECs following co-culture with rat astrocytes (700 $\Omega \times cm^2$), primary human NPC-derived neurons and astrocytes (450 $\Omega \times cm^2$), and primary pericytes followed by NPC-derived neurons and astrocytes (600 $\Omega \times cm^2$) (Lippmann et al. 2012, Lippmann et al. 2014). It may be possible to further enhance iPSC-derived BMEC properties by including co-culture with iPSC-derived pericytes, although iPSC-derived pericytes with brain-specific attributes have not yet been reported (Kusuma et al. 2015, van der Meer et al. 2013). Additionally, manipulation of key BBB signaling pathways could be used to further enhance BBB properties, as we have previously demonstrated with retinoic acid enhancement of iPSC-derived BMEC properties in a pericyte, astrocyte and neuron co-culture model (Lippmann et al. 2014).

The major phenotypic change observed after co-culture was the improved barrier function as observed through TEER and reduced passive permeability. As described previously for hydrocortisone treated rat BMECs, significant changes were not observed in occludin or claudin-5 protein levels, suggesting the presence of sufficient tight junction protein for the observed barrier tightening (Calabria et al. 2006). Alternatively, previous studies have demonstrated a strong correlation between junctional continuity and barrier phenotype (Butt et al. 1990, Weidenfeller et al. 2007, Calabria et al. 2006, Weidenfeller et al. 2005, Lippmann et al. 2014, Nakagawa et al. 2009). Similar to these studies, upon co-culture with EZ-sphere-derived neurons and astrocytes, there was a significant reduction in the number of discontinuous junctions in iPSC-derived BMECs. These data indicate that tight junction continuity and not protein expression levels are likely responsible for the observed barrier induction upon co-culture. As another BBB phenotype that could potentially be influenced by co-culture, PGP efflux activity was evaluated. We have previously demonstrated that the iPSC-derived BMECs express functional efflux transporters including PGP, multidrug resistance protein and breast cancer resistance protein (Lippmann et al. 2012, Lippmann et al. 2014, Wilson et al. 2015, Stebbins et al. 2015). Similarly, the iPSC-derived BMECs generated in this study displayed PGP efflux function. Co-culture with EZ-sphere derived astrocytes and neurons had no substantial effect on PGP activity, nor did primary rat astrocyte or primary human NPC-derived astrocyte and neuron co-culture. While a number of studies have demonstrated that co-culture can enhance PGP protein expression and activity levels (Berezowski et al. 2004, Dohgu et al. 2005, Nakagawa et al. 2009, Perrière et al. 2007), other studies reported no changes in PGP expression or activity in immortalized or primary BBB co-culture models, similar to our observations (Freese et al. 2014, Lim et al. 2007). In addition, given their distinct differentiated origin, it is possible that the iPSC-derived BMECs already possess the appropriate cues for PGP expression unlike primary or immortalized BMEC lines. For instance, while retinoic acid addition can enhance PGP expression and activity in immortalized human and rat brain cell lines (Mizee et al. 2013, El Hafny et al. 1997), it did not change the PGP activity in iPSC-derived BMECs (Lippmann et al. 2014). Finally, co-culture with EZ-sphere-derived neurons and astrocytes (1:3) did not appear to affect other key BMEC characteristics such as the expression levels of Glut-1, MRP-1, BCRP, or TfR transporters.

Finally, we have created an isogenic BBB model where neurons, astrocytes, and BMECs were derived from the same human iPSC line. The isogenic BBB model performed similarly to the models that combined BMECs and EZ-spheres from different sources, and demonstrated elevated TEER and reduced permeability. Additionally, iPSC-derived BMEC co-culture with EZ-sphere-derived astrocytes and neurons resulted in a prolonged elevated TEER compared to previously described models employing primary rat astrocytes and primary human NPCs as co-cultured neural cell sources (Lippmann et al. 2012, Lippmann et al. 2014), thereby increasing the time window for model deployment. It is predicted that the development of such an isogenic BBB model will enable new applications for human BBB models. Specifically, the ability to investigate the impact of genetic human disease on BBB function could prove powerful. Additionally, an iPSC-derived BBB model could be deployed to analyze drug permeability on a patient-by-patient basis thereby contributing to a personalized medicine approach for those suffering with neurological disease.

REFERENCES

Azevedo, F. A., Carvalho, L. R., Grinberg, L. T., Farfel, J. M., Ferretti, R. E., Leite, R. E., Jacob Filho, W., Lent, R. and Herculano-Houzel, S. (2009) Equal numbers of neuronal and nonneuronal cells make the human brain an isometrically scaled-up primate brain. *J Comp Neurol,* 513, 532-541.

Berezowski, V., Landry, C., Dehouck, M. P., Cecchelli, R. and Fenart, L. (2004) Contribution of glial cells and pericytes to the mRNA profiles of P-glycoprotein and multidrug resistance-associated proteins in an in vitro model of the blood-brain barrier. *Brain Res,* 1018, 1-9.

Brown, J. A., Pensabene, V., Markov, D. A. et al. (2015) Recreating blood-brain barrier physiology and structure on chip: A novel neurovascular microfluidic bioreactor. *Biomicrofluidics,* 9, 054124.

Butt, A. M., Jones, H. C. and Abbott, N. J. (1990) Electrical resistance across the blood-brain barrier in anaesthetized rats: a developmental study. *J Physiol,* 429, 47-62.

Calabria, A. R. and Shusta, E. V. (2008) A genomic comparison of in vivo and in vitro brain microvascular endothelial cells. *J Cereb Blood Flow Metab,* 28, 135-148.

Calabria, A. R., Weidenfeller, C., Jones, A. R., de Vries, H. E. and Shusta, E. V. (2006) Puromycin-purified rat brain microvascular endothelial cell cultures exhibit improved barrier properties in response to glucocorticoid induction. *J Neurochem,* 97, 922-933.

Cecchelli, R., Berezowski, V., Lundquist, S., Culot, M., Renftel, M., Dehouck, M. P. and Fenart, L. (2007) Modelling of the blood-brain barrier in drug discovery and development. *Nat Rev Drug Discov,* 6, 650-661.

Deli, M. A., Abraham, C. S., Kataoka, Y. and Niwa, M. (2005) Permeability studies on in vitro blood-brain barrier models: physiology, pathology, and pharmacology. *Cell Mol Neurobiol,* 25, 59-127.

Dohgu, S., Takata, F., Yamauchi, A. et al. (2005) Brain pericytes contribute to the induction and up-regulation of blood-brain barrier functions through transforming growth factor-beta production. *Brain Res,* 1038, 208-215.

Ebert, A. D., Shelley, B. C., Hurley, A. M. et al. (2013) EZ spheres: a stable and expandable culture system for the generation of pre-rosette multipotent stem cells from human ESCs and iPSCs. *Stem Cell Res,* 10, 417-427.

El Hafny, B., Chappey, O., Piciotti, M., Debray, M., Boval, B. and Roux, F. (1997) Modulation of P-glycoprotein activity by glial factors and retinoic acid in an immortalized rat brain microvessel endothelial cell line. *Neurosci Lett,* 236, 107-111.

Freese, C., Reinhardt, S., Hefner, G., Unger, R. E., Kirkpatrick, C. J. and Endres, K. (2014) A novel blood-brain barrier co-culture system for drug targeting of Alzheimer's disease: establishment by using acitretin as a model drug. *PLoS One,* 9, e91003.

Förster, C., Burek, M., Romero, I. A., Weksler, B., Couraud, P. O. and Drenckhahn, D. (2008) Differential effects of hydrocortisone and TNFalpha on tight junction proteins in an in vitro model of the human blood-brain barrier. *J Physiol,* 586, 1937-1949.

Herculano-Houzel, S. and Lent, R. (2005) Isotropic fractionator: a simple, rapid method for the quantification of total cell and neuron numbers in the brain. *J Neurosci,* 25, 2518-2521.

Janzer, R. C. and Raff, M. C. (1987) Astrocytes induce blood-brain barrier properties in endothelial cells. *Nature,* 325, 253-257.

Kim, J. E., O'Sullivan, M. L., Sanchez, C. A. et al. (2011) Investigating synapse formation and function using human pluripotent stem cell-derived neurons. *Proc Natl Acad Sci USA,* 108, 3005-3010.

Krencik, R. and Zhang, S. C. (2011) Directed differentiation of functional astroglial subtypes from human pluripotent stem cells. *Nat Protoc,* 6, 1710-1717.

Kusuma, S., Facklam, A. and Gerecht, S. (2015) Characterizing human pluripotent-stem-cell-derived vascular cells for tissue engineering applications. *Stem Cells Dev,* 24, 451-458.

Lim, J. C., Wolpaw, A. J., Caldwell, M. A., Hladky, S. B. and Barrand, M. A. (2007) Neural precursor cell influences on blood-brain barrier characteristics in rat brain endothelial cells. *Brain Res,* 1159, 67-76.

Lippmann, E. S., Al-Ahmad, A., Azarin, S. M., Palecek, S. P. and Shusta, E. V. (2014) A retinoic acid-enhanced, multicellular human blood-brain barrier model derived from stem cell sources. *Sci Rep,* 4, 4160.

Lippmann, E. S., Al-Ahmad, A., Palecek, S. P. and Shusta, E. V. (2013) Modeling the blood-brain barrier using stem cell sources. *Fluids Barriers CNS,* 10, 2.

Lippmann, E. S., Azarin, S. M., Kay, J. E., Nessler, R. A., Wilson, H. K., Al-Ahmad, A., Palecek, S. P. and Shusta, E. V. (2012) Derivation of blood-brain barrier endothelial cells from human pluripotent stem cells. *Nat Biotechnol,* 30, 783-791.

Lippmann, E. S., Weidenfeller, C., Svendsen, C. N. and Shusta, E. V. (2011) Blood-brain barrier modeling with co-cultured neural progenitor cell-derived astrocytes and neurons. *J Neurochem,* 119, 507-520.

Man, S., Ubogu, E. E., Williams, K. A., Tucky, B., Callahan, M. K. and Ransohoff, R. M. (2008) Human brain microvascular endothelial cells and umbilical vein endothelial cells differentially facilitate leukocyte recruitment and utilize chemokines for T cell migration. *Clin Dev Immunol,* 2008, 384982.

Mizee, M. R., Wooldrik, D., Lakeman, K. A. et al. (2013) Retinoic acid induces blood-brain barrier development. *J Neurosci,* 33, 1660-1671.

Nakagawa, S., Deli, M. A., Kawaguchi, H., Shimizudani, T., Shimono, T., Kittel, A., Tanaka, K. and Niwa, M. (2009) A new blood-brain barrier model using primary rat brain endothelial cells, pericytes and astrocytes. *Neurochem Int,* 54, 253-263.

Nakagawa, S., Deli, M. A., Nakao, S., Honda, M., Hayashi, K., Nakaoke, R., Kataoka, Y. and Niwa, M. (2007) Pericytes from brain microvessels strengthen the barrier integrity in primary cultures of rat brain endothelial cells. *Cell Mol Neurobiol,* 27, 687-694.

Perrière, N., Yousif, S., Cazaubon, S. et al. (2007) A functional in vitro model of rat blood-brain barrier for molecular analysis of efflux transporters. *Brain Res,* 1150, 1-13.

Sareen, D., Gowing, G., Sahabian, A. et al. (2014) Human induced pluripotent stem cells are a novel source of neural progenitor cells (iNPCs) that migrate and integrate in the rodent spinal cord. *J Comp Neurol,* 522, 2707-2728.

Savettieri, G., Di Liegro, I., Catania, C. et al. (2000) Neurons and ECM regulate occludin localization in brain endothelial cells. *Neuroreport,* 11, 1081-1084.

Schiera, G., Bono, E., Raffa, M. P., Gallo, A., Pitarresi, G. L., Di Liegro, I. and Savettieri, G. (2003) Synergistic effects of neurons and astrocytes on the differentiation of brain capillary endothelial cells in culture. *J Cell Mol Med,* 7, 165-170.

Schiera, G., Sala, S., Gallo, A., Raffa, M. P., Pitarresi, G. L., Savettieri, G. and Di Liegro, I. (2005) Permeability properties of a three-cell type in vitro model of blood-brain barrier. *J Cell Mol Med,* 9, 373-379.

Stebbins, M. J., Wilson, H. K., Canfield, S. G., Qian, T., Palecek, S. P. and Shusta, E. V. (2015) Differentiation and characterization of human pluripotent stem cell-derived brain microvascular endothelial cells. *Methods.*

Syvänen, S., Lindhe, O., Palner, M., Kornum, B. R., Rahman, O., Långström, B., Knudsen, G. M. and Hammarlund-Udenaes, M. (2009) Species differences in blood-brain barrier transport of three positron emission tomography radioligands with emphasis on P-glycoprotein transport. *Drug Metab Dispos,* 37, 635-643.

van der Meer, A. D., Orlova, V. V., ten Dijke, P., van den Berg, A. and Mummery, C. L. (2013) Three-dimensional co-cultures of human endothelial cells and embryonic stem cell-derived pericytes inside a microfluidic device. *Lab Chip,* 13, 3562-3568.

Warren, M. S., Zerangue, N., Woodford, K. et al. (2009) Comparative gene expression profiles of ABC transporters in brain microvessel endothelial cells and brain in five species including human. *Pharmacol Res,* 59, 404-413.

Weidenfeller, C., Schrot, S., Zozulya, A. and Galla, H. J. (2005) Murine brain capillary endothelial cells exhibit improved barrier properties under the influence of hydrocortisone. *Brain Res,* 1053, 162-174.

Weidenfeller, C., Svendsen, C. N. and Shusta, E. V. (2007) Differentiating embryonic neural progenitor cells induce blood-brain barrier properties. *J Neurochem,* 101, 555-565.

Weksler, B. B., Subileau, E. A., Perrière, N. et al. (2005) Blood-brain barrier-specific properties of a human adult brain endothelial cell line. *FASEB J,* 19, 1872-1874.

Wilson, H. K., Canfield, S. G., Hjortness, M. K., Palecek, S. P. and Shusta, E. V. (2015) Exploring the effects of cell seeding density on the differentiation of human pluripotent stem cells to brain microvascular endothelial cells. *Fluids Barriers CNS,* 12, 13.

Yu, J. Y., Vodyanik, M. A., Smuga-Otto, K. et al. (2007) Induced pluripotent stem cell lines derived from human somatic cells. *Science,* 318, 1917-1920.

Zhao, Z., Nelson, A. R., Betsholtz, C. and Zlokovic, B. V. (2015) Establishment and Dysfunction of the Blood-Brain Barrier. *Cell,* 163, 1064-1078.

Zlokovic, B. V. (2008) The blood-brain barrier in health and chronic neurodegenerative disorders. *Neuron,* 57, 178-201.

We claim:

1. A method of inducing blood brain barrier properties in induced pluripotent stem cell (iPSC)-derived brain microvascular endothelial cells (BMECs) so as to generate an isogenic blood brain barrier model comprising the steps of:
   (a) co-culturing iPSC-derived BMECs on a permeable membrane with a combination of iPSC-derived astrocytes and iPSC-derived neurons;
   wherein
   (i) the permeable membrane separates the BMECs from the astrocytes and neurons,
   (ii) the neurons and astrocytes are derived from EZ-spheres differentiated from iPSCs,
   (iii) blood brain barrier properties are induced in the BMECs to form the isogenic blood brain barrier model,
   (iv) the iPSC-derived astrocytes and iPSC-derived neurons are isogenic to the iPSC-derived BMECs and all three cell types are derived from the same iPSC cell population,
   (v) the ratio of neurons to astrocytes in the co-culture is 1:3, and
   (vi) the trans-endothelial electrical resistance (TEER) of the isogenic blood brain barrier model is between 700-900 $\Omega \times cm^2$ and is maintained for at least 5 days.

2. An isogenic blood brain barrier model created by the method of claim 1, wherein the
   iPSC-derived astrocytes express glial fibrillary acidic protein and S100 calcium binding protein B, and the iPSC-derived neurons expressing β-tubulin III.

3. The blood brain barrier of claim 2, wherein the permeability is less than $2 \times 10^{-7}$ cm/s.

4. The blood brain barrier of claim 2, wherein the percentage of discontinuous junctions is less than 2%.

5. The method of claim 1, wherein the neurons are created by a method of differentiating induced pluripotent stem cells (iPSC) to neurons, the method comprising the steps of:
   i) differentiating the iPSCs into EZ-spheres;
   ii) singularizing the EZ-spheres;
   iii) seeding the singularized EZ-spheres on to an extracellular matrix; and
   iv) culturing the seeded EZ-spheres in a neural medium, wherein neurons are formed, and wherein the neurons express β-tubulin III.

6. The method of claim 5, wherein the seeding density is 20,000-30,000 cell/cm$^2$.

7. The method of claim 5, wherein step (iv) lasts 14 days.

8. The method of claim 1, wherein the astrocytes are created by a method of differentiating induced pluripotent stem cells (iPSC) to astrocytes, the method comprising the steps of:
   i) differentiating the iPSCs into EZ-spheres;
   ii) treating the EZ-spheres with a neural induction medium to produce astro-spheres;
   iii) culturing the astro-spheres, wherein the cells are passaged weekly;
   iv) singularizing the astro-spheres;
   v) seeding the singularized astro-spheres on an extracellular matrix; and
   vi) culturing the seeded astro-spheres in medium comprising DMEM/F12, NEAA, N2 and heparin, wherein astrocytes are formed, and wherein astrocytes express glial fibrillary acidic protein and S 100 calcium binding protein B.

9. The method of claim 8 wherein the seeding density is 20,000-30,000 cell/cm'.

10. The method of claim 8, wherein step (ii) lasts 11 days.

11. The method of claim 8, wherein step (vi) lasts 14 days.

12. A method of inducing blood brain barrier properties in induced pluripotent stem cell (iPSC)-derived brain microvascular endothelial cells (BMECs) so as to generate an isogenic blood brain barrier model comprising the steps of co-culturing iPSC-derived BMECs with a combination of iPSC-derived astrocytes and iPSC-derived neurons; wherein the BMECs are cultured on a permeable membrane, the permeable membrane separating the BMECs from the astrocytes and neurons, wherein blood brain barrier properties are induced in the BMECs, wherein the ratio of neurons to astrocytes in the co-culture is 1:3±10%, wherein the trans-endothelial electrical resistance (TEER) is between 700-900 $\Omega \times cm^2$ and is maintained for at least 5 days, and wherein the percentage of discontinuous junctions is less than 8% in the BMEC layer.

13. The method of claim 12, wherein the neurons are created by a method of differentiating induced pluripotent stem cells (iPSC) to neurons, the method comprising the steps of:
   i) differentiating the iPSCs into EZ-spheres;
   ii) singularizing the EZ-spheres;
   iii) seeding the singularized EZ-spheres on to an extracellular matrix; and
   iv) culturing the seeded EZ-spheres in a neural medium, wherein neurons are formed, and wherein the neurons express β-tubulin III.

14. The method of claim 13, wherein the seeding density is 20,000-30,000 cell/cm$^2$.

15. The method of claim 13, wherein step (iv) lasts 14 days.

16. The method of claim 12, wherein the astrocytes are created by a method of differentiating induced pluripotent stem cells (iPSC) to astrocytes, the method comprising the steps of:
   i) differentiating the iPSCs into EZ-spheres;
   ii) treating the EZ-spheres with a neural induction medium to produce astro-spheres;

iii) culturing the astro-spheres, wherein the cells are passaged weekly;
iv) singularizing the astro-spheres;
v) seeding the singularized astro-spheres on an extracellular matrix; and
vi) culturing the seeded astro-spheres in medium comprising DMEM/F12, NEAA, N2 and heparin, wherein astrocytes are formed, and wherein astrocytes express glial fibrillary acidic protein and S100 calcium binding protein B.

17. The method of claim 16, wherein the seeding density is 20,000-30,000 cell/cm$^2$.

18. The method of claim 16, wherein step (ii) lasts 11 days.

19. The method of claim 16, wherein step (vi) lasts 14 days.

20. An isogenic blood brain barrier model created by the method of claim 12, wherein the iPSC-derived astrocytes express glial fibrillary acidic protein and S100 calcium binding protein B and the iPSC-derived neurons express β-tubulin III, and wherein the iPSC-derived astrocytes and iPSC-derived neurons are isogenic to the iPSC-derived BMECs and are derived from the same iPSC cell population.

21. The blood brain barrier of claim 20, wherein the permeability is less than $2\times10^{-7}$ cm/s.

22. The blood brain barrier of claim 20, wherein the percentage of discontinuous junctions is less than 2%.

23. The blood brain barrier of claim 2, wherein the percentage of discontinuous junctions is less than 5%.

24. The blood brain barrier of claim 2, wherein the percentage of discontinuous junction is less than 3%.

25. The blood brain barrier of claim 20, wherein the percentage of discontinuous junctions is less than 5%.

26. The blood brain barrier of claim 20, wherein the percentage of discontinuous junctions is less than 3%.

* * * * *

UNITED STATES PATENT AND TRADEMARK OFFICE
CERTIFICATE OF CORRECTION

PATENT NO. : 11,840,708 B2  
APPLICATION NO. : 16/091450  
DATED : December 12, 2023  
INVENTOR(S) : Eric V. Shusta et al.

Page 1 of 1

It is certified that error appears in the above-identified patent and that said Letters Patent is hereby corrected as shown below:

In the Specification

Column 1, Line 7, "application claims" should be --application is a 371 U.S. National Phase Entry of PCT/US2017/025935, filed April 4, 2017, which claims--.

Column 1, Line 8, "2016, which" should be --2016, each of which--.

Column 11, Line 20, "CSO3iCTRn2" should be --CS03iCTRn2--.

Column 11, Line 24, "CSO3iCTRn2'" should be --CS03iCTRn2--.

Column 11, Line 54, "CSO3iCTRn2'" should be --CS03iCTRn2--.

In the Claims

Column 23, Line 58, "expressing" should be --express--.

Signed and Sealed this  
Twenty-seventh Day of August, 2024

Katherine Kelly Vidal  
*Director of the United States Patent and Trademark Office*